US011847936B2

(12) United States Patent
Jarc et al.

(10) Patent No.: US 11,847,936 B2
(45) Date of Patent: Dec. 19, 2023

(54) TRAINING USERS USING INDEXED TO MOTION PICTURES

(71) Applicant: Intuitive Surgical Operations, Inc., Sunnyvale, CA (US)

(72) Inventors: Anthony M. Jarc, Duluth, GA (US); Liheng Guo, Duluth, GA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 392 days.

(21) Appl. No.: 17/293,005

(22) PCT Filed: Nov. 15, 2019

(86) PCT No.: PCT/US2019/061879
§ 371 (c)(1),
(2) Date: May 11, 2021

(87) PCT Pub. No.: WO2020/102773
PCT Pub. Date: May 22, 2020

(65) Prior Publication Data
US 2021/0407309 A1 Dec. 30, 2021

Related U.S. Application Data

(60) Provisional application No. 62/767,872, filed on Nov. 15, 2018.

(51) Int. Cl.
*G09B 5/02* (2006.01)
*G09B 19/24* (2006.01)
(Continued)

(52) U.S. Cl.
CPC .............. *G09B 5/02* (2013.01); *G06F 3/011* (2013.01); *G06F 3/0346* (2013.01);
(Continued)

(58) Field of Classification Search
CPC ........ A61B 90/37; A61B 90/36; G09B 19/24; G09B 23/28; G09B 23/30; G09B 23/285; G09B 23/286
See application file for complete search history.

(56) References Cited

U.S. PATENT DOCUMENTS

| 10,791,301 B1* | 9/2020 | Garcia Kilroy ........ G16H 70/20 |
| 2008/0145830 A1* | 6/2008 | Huang ..................... G09B 9/00 434/336 |

(Continued)

FOREIGN PATENT DOCUMENTS

WO WO-2018089816 A2 5/2018

OTHER PUBLICATIONS

International Preliminary Report on Patentability for Application No. PCT/US2019/061879, dated May 27, 2021, 18 pages.
(Continued)

*Primary Examiner* — Robert J Utama
(74) *Attorney, Agent, or Firm* — Foley & Lardner LLP

(57) ABSTRACT

A system includes a sensor to sense a change in a position of an input control component and a tool; a storage medium embodies a collection of respective motion pictures, which show tool movement imparted by the control component in response to manual input provided by users, indexed based upon a metric; a storage medium embodies a set of instructions that cause a processor to perform operations comprising: determining a user's performance; recording a motion picture of the tool movement imparted by the master control component by the individual user; indexing the recorded motion picture to the collection of motion pictures; generating a user interface providing an interactive visual index; and displaying a selected motion picture on the display screen in response to user input at the interactive visual index.

20 Claims, 17 Drawing Sheets

(51) Int. Cl.
  *G16H 40/63* (2018.01)
  *G16H 70/20* (2018.01)
  *G06F 3/01* (2006.01)
  *G06F 3/0346* (2013.01)
  *G06F 3/0482* (2013.01)
  *H04N 5/76* (2006.01)
  *A61B 34/37* (2016.01)

(52) U.S. Cl.
  CPC ........... *G06F 3/0482* (2013.01); *G09B 19/24* (2013.01); *G16H 40/63* (2018.01); *G16H 70/20* (2018.01); *H04N 5/76* (2013.01); *A61B 34/37* (2016.02)

(56) References Cited

U.S. PATENT DOCUMENTS

| 2014/0220527 | A1* | 8/2014 | Li | G06V 20/10 |
| | | | | 434/262 |
| 2014/0287393 | A1* | 9/2014 | Kumar | G09B 5/02 |
| | | | | 434/262 |
| 2017/0053543 | A1 | 2/2017 | Agrawal et al. | |
| 2017/0300752 | A1* | 10/2017 | Biswas | G09B 5/02 |

OTHER PUBLICATIONS

International Search Report and Written Opinion for Application No. PCT/US2019/061879, dated Feb. 13, 2020, 20 pages.

Jarc A.M., et al., Viewpoint Matters: Objective Performance Metrics for Surgeon Endoscope Control during Robot-assisted Surgery, Surgical Endoscopy, 2017, vol. 31 (3), pp. 1192-1202.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

TRAINING USERS USING INDEXED TO MOTION PICTURES

CLAIM OF PRIORITY

This application is a U.S. National Stage Filing under 35 U.S.C. 371 from International Application No. PCT/US2019/061879, filed on Nov. 15, 2019, and published as WO 2020/102773 A1 on May 22, 2020, which claims the benefit of priority to U.S. Provisional Patent Application No. 62/767,872, filed on Nov. 15, 2018, each of which is incorporated by reference herein in its entirety.

BACKGROUND

Ongoing surgeon training and practice in surgical techniques is crucial to achieving and maintaining and improving surgical skill. Traditional approaches to training surgeons are being challenged by rapid advances in technology that enable capture and analysis of large quantities of complex surgical data. Surgeons may learn robot-assisted minimally invasive surgery by performing inanimate practice tasks with clinical robots. Expert surgeons are commonly asked to evaluate these performances using standardized scales, but doing such ratings may time consuming, tedious, and subjective.

SUMMARY

In one aspect, a system is provided that includes a memory storage device embodies a collection of respective motion pictures, which respectively show slave tool movement controlled by user input received at the master control component input from corresponding respective users, indexed based upon corresponding respective user performance for a metric of the corresponding respective users controlling the slave tool movement shown in respective motion pictures. The motion pictures also may show not only movements of the instruments inside a patient, but also, may show the patient anatomy, any interactions between the tools/tissue. The system includes a hardware processor and a display screen. A memory storage device embodies a set of instructions that, when executed by the at least one hardware processor, cause the at least one processor to perform operations. The operations include generating a user interface on the display screen providing an interactive visual index to select respective motion pictures from the collection of respective motion pictures based upon corresponding respective user performance for the metric of corresponding respective users that controlled tool movement shown in the respective motion pictures The operations also include selecting a motion picture from the collection of motion pictures in response to receiving user input indicating an index point.

DESCRIPTION OF EMBODIMENTS

Minimally Invasive Surgical System

Figure 1:
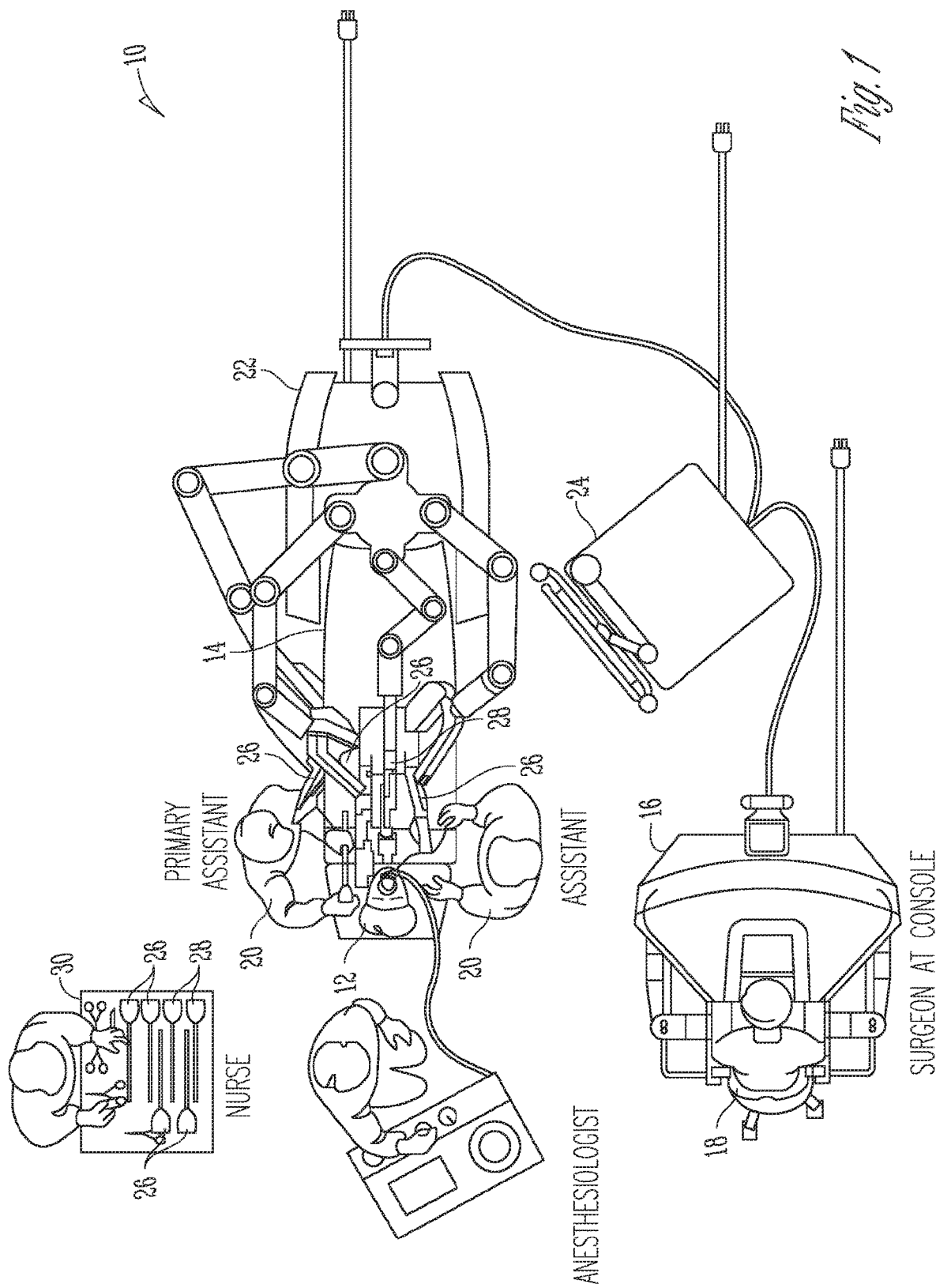
FIG. 1 is an illustrative plan view of a system for performing a minimally invasive diagnostic or surgical procedure.

FIG. 1 is an illustrative plan view of a system 10 for performing a minimally invasive diagnostic or surgical procedure on a patient 12 who is lying on an operating table 14. The system 10 includes a control console 16 for use by a user 18, such as a surgeon, during a procedure such as an actual or simulated diagnostic or surgical procedure. An actual surgical or diagnostic procedure may involve a surgical setting within a patient's anatomy. A simulated surgical procedure may involve a simulated surgical setting that simulates a patients anatomy. One or more assistants 20 may also participate in the procedure. The system 10 further includes a manipulator system 22 that may be mounted on a portable patient-side cart and an electronics system 24 that may be mounted on a portable electronics cart. The manipulator system 22 can manipulate one or more tools 26 through a minimally invasive incision in the body of the patient 12 while the user 18 views a procedure site through an image viewer display at the control console 16. In a surgical or diagnostic context, tools 26 may include both those with tissue interaction functions (e.g., graspers, scissors, cautery hooks, needles, electrocautery devices, staplers, clip appliers) and those with sensing functions such as imaging (e.g., endoscopes, ultrasound probes, OCT probes). One or more tools may be manipulated within a surgical site during a procedure. An image of the procedure site can be obtained by a steerable imaging capture tool 28, such as an endoscope, particularly a stereoscopic endoscope, which may be manipulated by the manipulator system 22 to orient the imaging capture tool e 28. The electronics system 24 includes computer processors that may be used to process the images of the surgical site captured by the image capture tool 28 for subsequent display to a user 18 through the control console 16. In some embodiments, stereoscopic images may be captured, which allow the perception of depth during a procedure. The number of tools 26 used together during a procedure will generally depend on the type of procedure such as a diagnostic or surgical procedure and the space constraints within the procedure site among other factors. If it is necessary to change one or more of the tools 26 being used during a procedure, an assistant 20 may remove the tool 26 from the manipulator system 22, and replace it with another tool 26 from a tray 30 in an operating room, for example.

Figure 2:
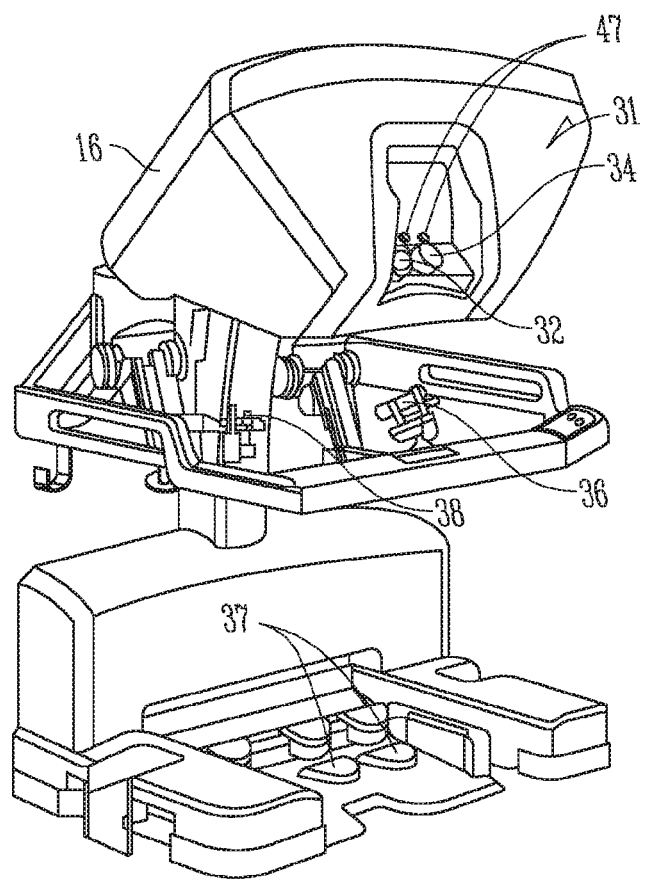
FIG. 2 is a perspective view of the control console of the system of FIG. 1.

FIG. 2 is a perspective view of the control console 16. The control console 16 includes a viewer display 31 that includes a left eye display 32 and a right eye display 34 for presenting the user 18 with a coordinated stereoscopic view of the procedure site that enables depth perception. The console 16 further includes right and left manually operated hand-operated master control inputs 36, 38 to receive larger-scale hand control movements and includes one or more manually operated clutch controls, 37 which may include one or more manually operated foot pedals. More particularly, in some embodiments there is a master clutch foot pedal that clutches the master controllers so that they can move without the instruments moving (akin picking a mouse up off of the table to recenter a cursor for example). This is for ergonomic adjustments of the surgeon's hands/arms. There is another pedal to go into camera control mode so that the surgeon's hands move the viewpoint rather than move the instruments when it is pressed and held. There is another pedal to swap to a third arm. In some embodiments, there are four additional pedals to control bipolar and monopolar energy on the left and right instruments for cauterization, for example. One or more slave tools installed for use on the manipulator system 22 move in smaller-scale distances in response to surgeon 18's larger-scale manipulation of the one or more control inputs 36, 38. The control inputs 36, 38 may include grip members that include handles with finger loops and also may include trigger-like actuation members to actuate a tool such as by causing opening or closing of jaws of an end effector, for example. The control inputs 36, 38 are operatively coupled through kinematics, for example, to control motion of one or more tools 26 coupled to the manipulator system 22. The control inputs 36, 38 may provide the same mechanical degrees of freedom as their associated tools 26 to provide the user 18 with telepresence, or the perception that the control inputs 36 are integral with the tools 26 so that the user has a strong sense of directly controlling the tools 26. To this end, position, force, and tactile feedback sensors (not shown) may be employed to transmit position, force, and tactile sensations from the tools 26 back to the user's hands through the control inputs 36, 38, subject to communication delay constraints. A head-in sensor 47 provides an indication to the system 10 of whether the surgeon is looking into the display. The system may take actions accordingly, e.g. it may disable instrument control when the surgeon is not looking into the display to prevent unintentional movement.

Figure 3:
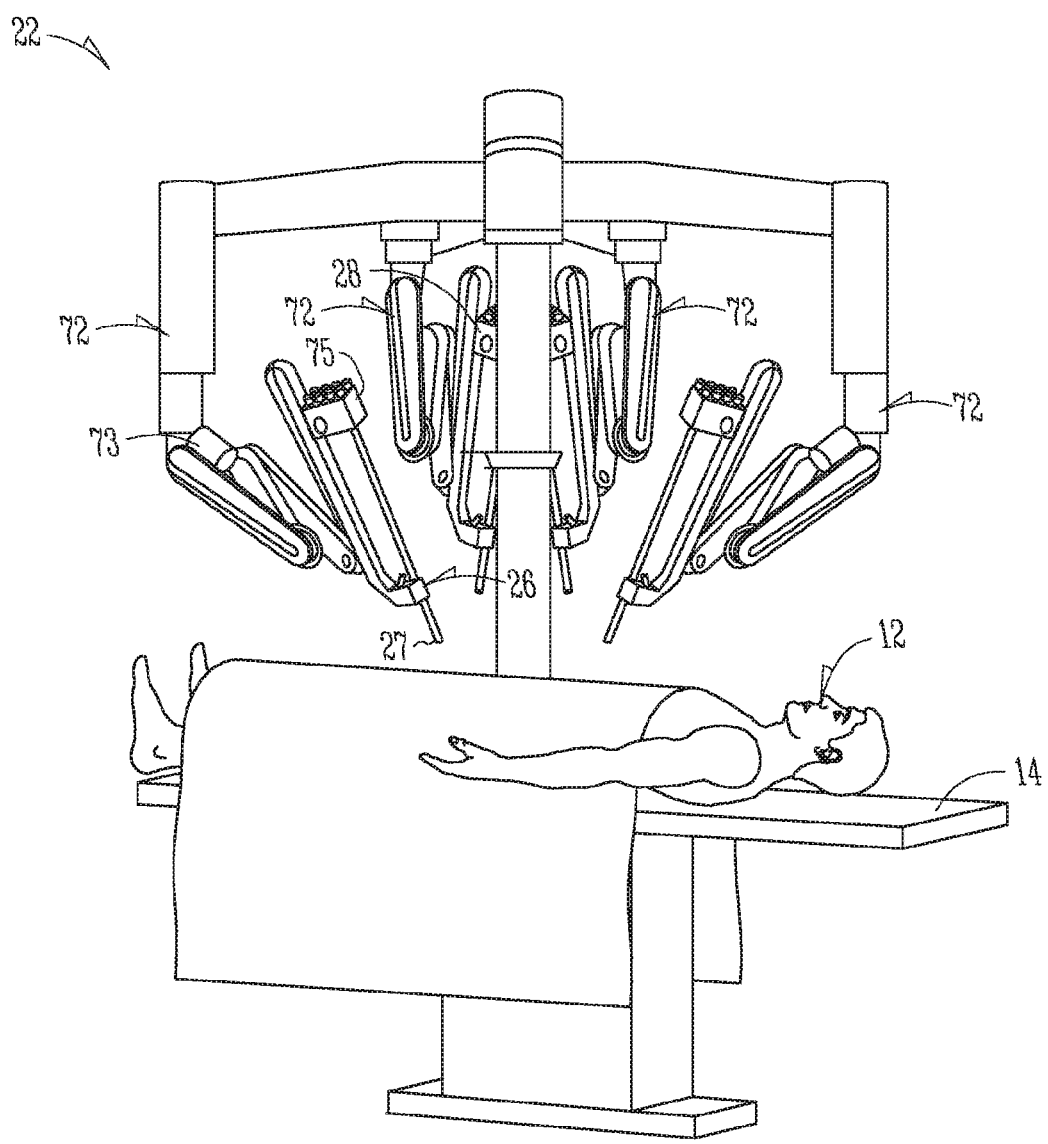
FIG. 3 is a perspective view of the manipulator system of the system of FIG. 1.

FIG. 3 is a perspective view of a manipulator system 22 of a minimally invasive surgical system 10. The manipulator system 22 includes four mechanical support arms 72. A tool manipulator 73, which includes motors to control tool motion, is mounted at the end of each support arm 72. Additionally, each support arm 72 can optionally include one or more setup joints (e.g., unpowered and/or lockable) that are used to position the attached tool manipulator 73 in relation to the patient for surgery. While the manipulator system 22 is shown as including four support arms 72 and corresponding tool manipulators 73, more or fewer support arms 72 and tool manipulators 73 may be used. A system 10 will generally include a vision system that typically includes an imaging capture tool device, 28 such as an endoscopic camera 28 for capturing motion picture images, such as video images. A system 10 also typically includes one or more motion picture displays, such as video displays, for displaying the captured motion picture images.

In some embodiments, movement of a slave tool 26/28 is controlled to mimic movements manually imparted to one or more of master control inputs 36, 38 such that the tool's movement follows the master's motion. Thus, user inputs provided at the control console 16 to control either a tool 26/28 as a whole or a tool's sub-components are such that the input provided at the control console 16 by a user, such as a surgeon or other medical person, to the control input (e.g., a "master" command) is translated into a corresponding action by the tool (e.g., a "slave" response). Thus, for example, user hand and/or finger movement received at one or more of the right and left manually operated hand-operated control inputs 36, 38 controls one or more corresponding tools 26/28 to move in a movement path that follows the user hand movement received at the control inputs 36, 38.

Figure 4:
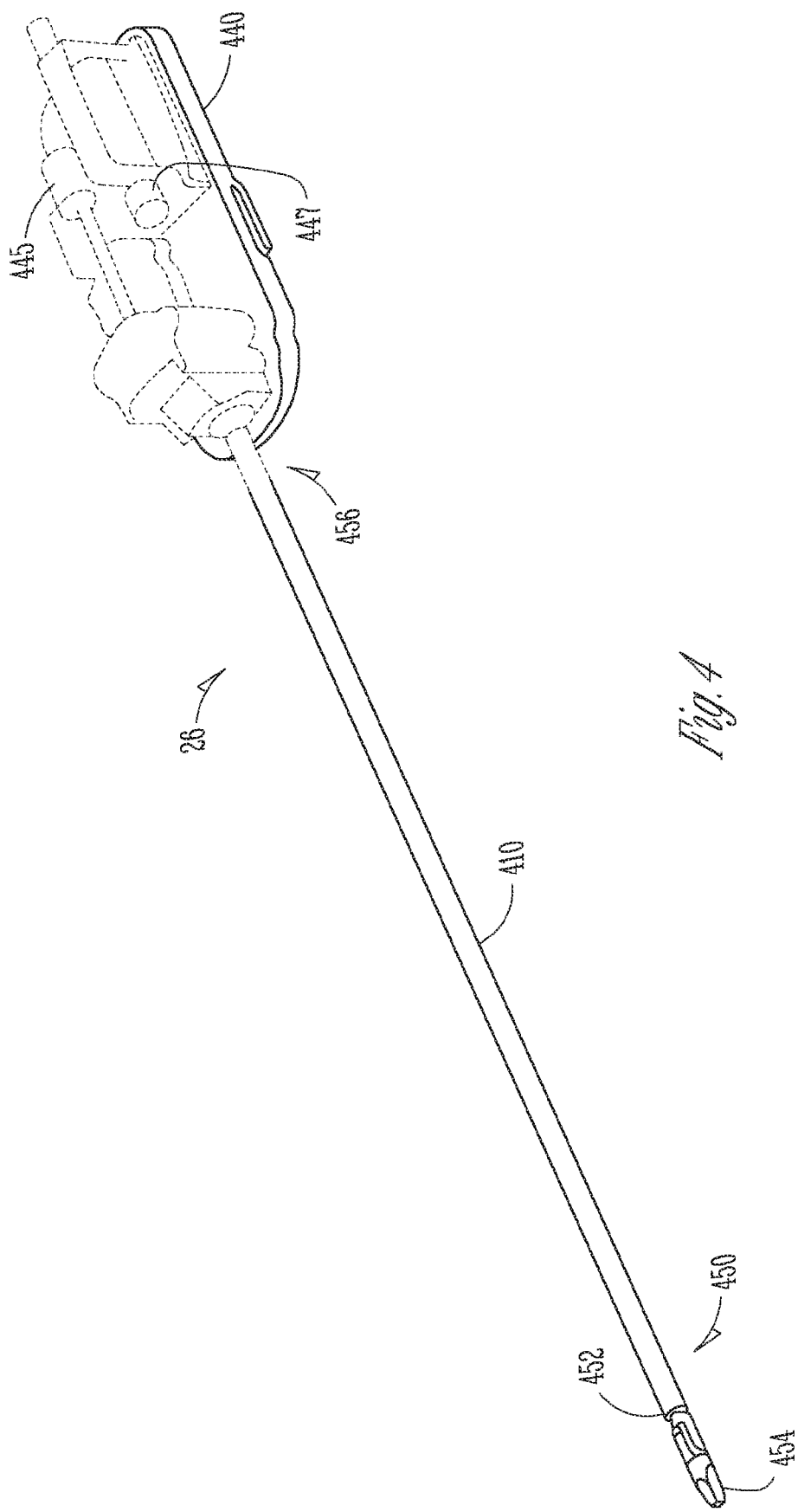
FIG. 4 is a perspective view of a tool of the system of FIG. 1.

FIG. 4 is a perspective view of a tool 26, which includes an elongated hollow tubular shaft 410 having a centerline longitudinal axis 411, a distal (first) end portion 450, which may be used for insertion into a patient's body cavity and proximal (second) end portion 456 coupled adjacent a control mechanism 440 that includes multiple actuator motors 445, 447 (shown with dashed lines) that exert force upon wire cables coupled to impart motion to the end effector 454 such as opening or closing of jaws and (x, y) wrist motion of a wrist. The tool 26 is used to carry out surgical or diagnostic procedures. The distal portion 450 of the tool 26 can include any of a variety of end effectors 454, such as the forceps shown, a needle driver, a cautery device, a cutting tool, an imaging device (e.g., an endoscope or ultrasound probe), or the like. The surgical end effector 454 can include a functional mechanical degree of freedom, such as jaws that open or close, or a knife that translates along a path or a wrist that may move in x and y directions. In the embodiment shown, the end effector 454 is coupled to the elongated hollow shaft 410 by a wrist 452 that allows the end effector to be oriented relative to the elongate tube centerline axis 411. The control mechanism 440 controls movement of the overall tool and the end effector at its distal portion.

Figure 5:
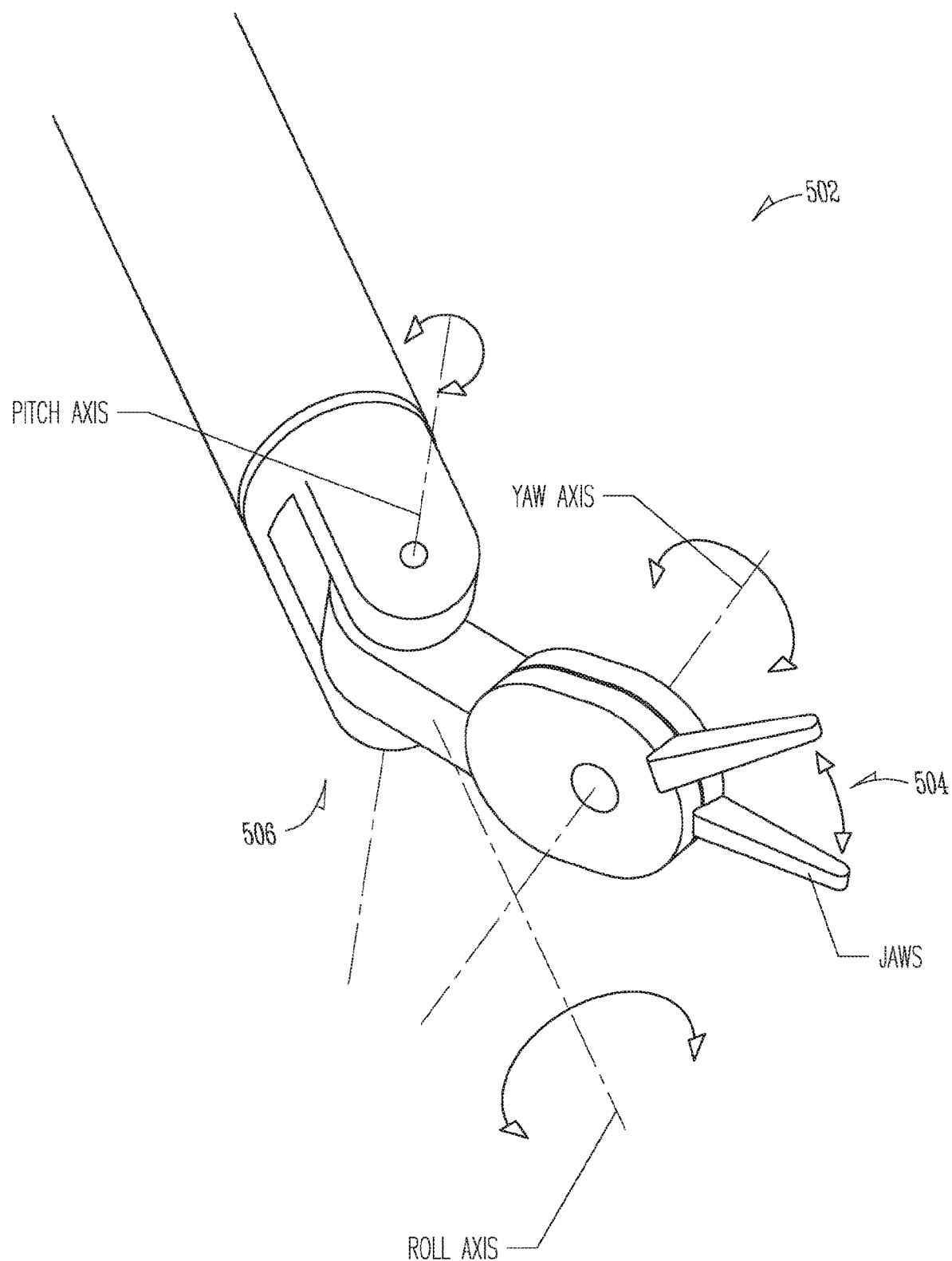
FIG. 5 is an illustrative perspective view of an end effector of the system of FIG. 1 that includes jaws and a wrist portion configured to provide rotation of the jaws about three axes.

FIG. 5 is an illustrative perspective view of an end effector 502 that includes jaws 504 and a wrist portion 506 configured to provide rotation of the jaws 504 about three axes. The end effector 502 is mounted to a distal end of a shaft 410. The jaws 504 are moveable between opened and closed positions in response to corresponding movement imparted by a user to the control inputs 36, 38. The wrist provides rotation about first, second and third (e.g., pitch, yaw and roll) axes in response to corresponding rotational movement imparted by a user to the control inputs 36, 38.

Capturing and Storing Motion Pictures

Figure 6:
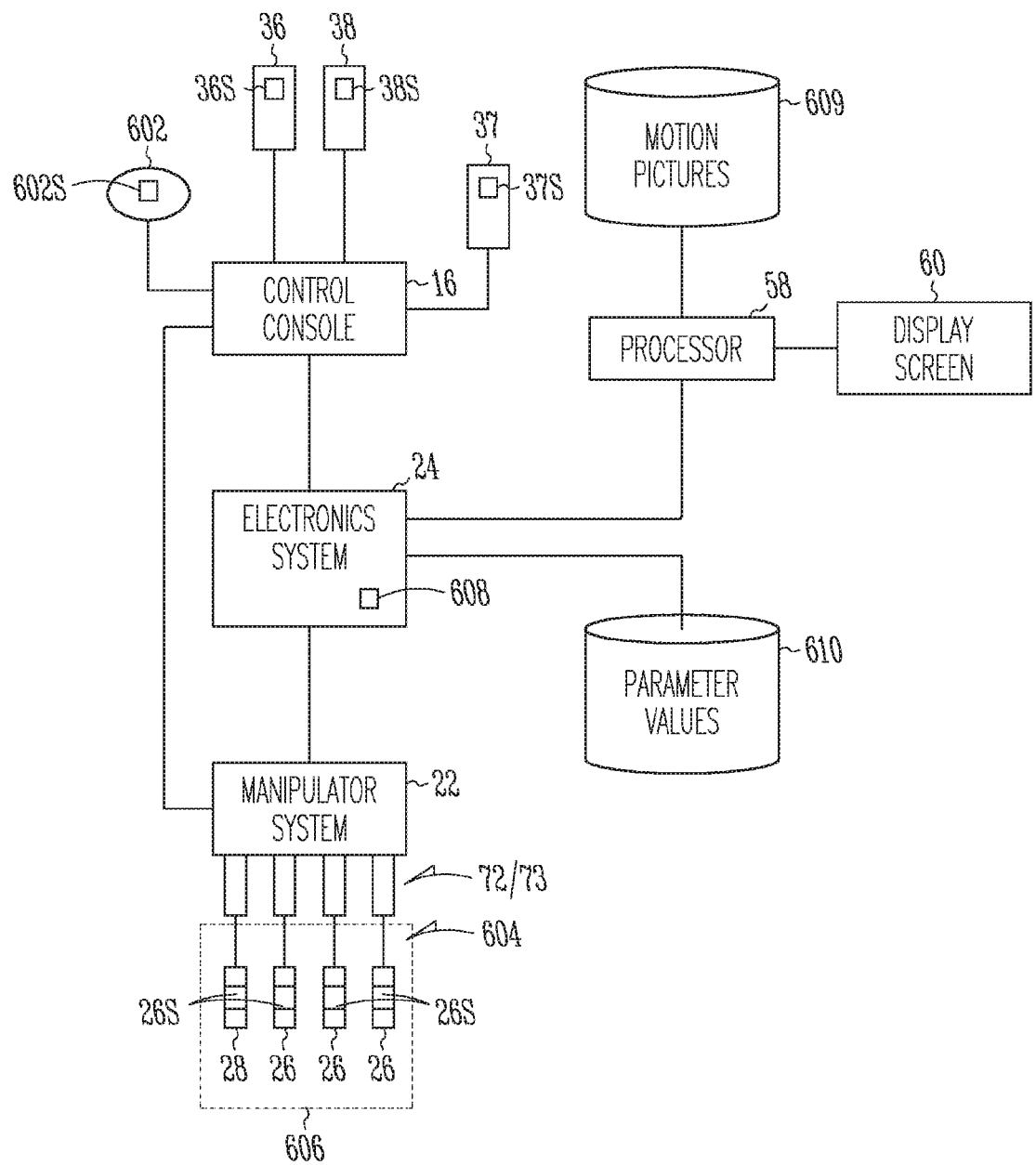
FIG. 6 is an illustrative functional block diagram of the system of FIG. 1.

FIG. 6 is an illustrative functional block diagram to illustrate use of the system of FIG. 1 to capture and display motion picture images of tool movement and to capture parameter values representing movement of input control components and tools corresponding to the displayed motion picture images. The control console 16 can be used by a user to control the manipulator system 22 during a procedure. The manipulator system 22 can use an imaging tool 28, such as a stereoscopic endoscope, to capture images of a tool site and output the captured images to a computer processor system 608 located at the electronics system 24, which may store the motion pictures in a machine-readable storage device 609 that may include non-volatile memory. Alternatively, for example, the motion pictures and system data indicating system state and movement can be stored locally or stored remotely, such as in a cloud database or server in a hospital since the system 10 can be continuously connected to the internet. The computer processor system 608 includes a machine-readable storage device, which may include non-volatile memory, to store computer instructions to control operation of a computer processor. In one aspect, the computer processor system 608 can process the captured images in a variety of ways prior to any subsequent display. For example, in some embodiments the computer processor system 608 can overlay the captured images with a virtual control interface prior to displaying the combined images to the surgeon via the control console 16.

Additionally, or in the alternative, the captured images can undergo image processing by a computer processor 58 located outside of the electronics system 24. The manipulator system 22 outputs the captured images to computer processor 58 for image processing prior to display on the control console 16. In another aspect, captured images first undergo image processing by the computer processor 608 on electronics cart 24 and then undergo additional image processing by computer processor 58 prior to display at the viewer display 31 of the control console 16. The system 10 can include an optional display 60 coupled with the computer processor 58, such that motion picture images can be displayed on display 60 in addition to being displayed on the viewer display 31 of the control console 16. Alternatively, for example, images may be displayed in a sub-window on the viewer display 31, as a window tile. This way the surgeon preserves the endoscope image but has additional information below or on the side, such as a reference video, real-time patient vitals, etc.

Capturing and Storing Parameter Values

Still referring to FIG. 6, the control console 16 includes multiple input control components: the right and left manually operated hand-operated control inputs 36, 38; the manually operated foot pedal clutch control 37; and the head-in sensor 47. The manipulator system 24 includes respective support arms/tool manipulators 72/73 that may be coupled to respective tools 26/28 that may be disposed within a procedure setting 604, which indicated by dashed lines 606. The procedure setting 604 is a location where tools 26/28 operatively coupled to support arms/tool manipulators 72/73 operate under control of user input to one or more of the input control components. The procedure setting 604 may be inside an actual patient body or within an environment that simulates the inside of a patient's body, for example. An imaging tool 28 captures motion picture images of the procedure setting 604 that may be displayed during performance of a procedure at the viewer display 31 and at the optional display 60. Each input control component 36, 38, 37, 47 is associated with at least one position and/or orientation sensor to sense and to track user input imparted to control one or more tools 26. A first hand sensor 36S is coupled to sense user hand and/or finger input to the right hand-operated control input. A second hand sensor 38S is coupled to sense user hand and/or finger input to the left hand-operated control input 38. First and second hand sensors 36S, 38S produce one or more signals indicative of motion of the left and right control inputs in six degrees of freedom (dof). In some embodiments, each control inputs 36, 38 includes a series of mechanical linkages joined by rotational joints (not shown). The sensors 36A, 36B on these joints read the angular orientations of the joints. Knowing the angles and the length of each mechanical linkage, one or more processors 608 of the system 10 can calculate the position, orientation, and grip of each hand. A clutch control sensor 37S is coupled to sense user input to the clutch control 37, to determine each time the foot pedal is depressed and each time the foot pedal is released, for example. A clutch control sensor 37S produces one or more signals indicative of user input to actuate a clutch to reposition a surgeon's hands without moving the instruments patient-side. A head-in sensor 47 is coupled to sense a user placing his or her head in contact with a viewer display 31 to ensure the surgeon is looking at the endoscopic image in the viewer before allowing the surgeon to move his/her controllers and therefore instruments. The head-in sensor 47 may be a proximity sensor such as an infrared sensor, for example. The head-in sensor 4747S produces one or more signals indicative of user placing his or input in contact with a viewer display 31. Additional sensors include camera pedal to move the camera with the surgeon's hands. A third arm swap pedal to swap to control a different arm with one of the surgeon's hands. Energy pedals to deliver particular types of energy through the instruments. Additional features can be enabled via the touchscreen such as flipping an angled endoscope from 30 up to 30 down, enabling a tile-sized window, swapping controls from one console to another console (for example for a trainee), selecting digital zoom, etc.

The manipulator system 22 may be coupled to control multiple tools 26/28 coupled to respective support arms/tool manipulators 72/73. Each component tool 26/28 is associated with at least one position or/or orientation tool sensor 26S to sense and track motion imparted to the tool 26/28 in response to user input to one or more of the input control components 36, 38, 37, 47. Similar to control inputs 36 and 38, each joint in the mechanical linkage of each instrument arm has a sensor (e.g. encoders) that reports the joint's angular rotation (or linear extension if it's a prismatic joint), so that the system can calculate the precise position and orientation of each tool 26/28 using the combined sensor readings, for example. Each tool sensors 26S produces one or more signals indicative of motion of an associated tool in one or more of six degrees of freedom.

The electronics system 24 receives sensor signals produced by the input control component sensors 36S, 38S, 37S, 4747S that are indicative of user-imparted movement and/or actuation of one or more corresponding input control components 36, 38, 37, 47. The electronics system 24 receives sensor signals produced by the one or more tool sensors 26S that are indicative of movement and/or actuation of one or more corresponding tools 26/28 in response to user input to one or more of the input control components 36, 38, 37, 47. The electronics system 24 may process the input control component sensors sensor signals and the tool sensor signals to produce parameter values indicative of user performance levels for different performance metrics such as: economy of motion, master workspace range; camera movement frequency/efficiency; third arm swap duration, frequency; idle time period; tool speed; and wrist manipulation. The electronics system 24 stores the parameter values within a machine-readable storage device 610, which may include non-volatile memory.

Tables 1-7 provide example table information structures within the storage device 610 to store parameter values indicative of movement and/or actuation of input control components and/or tools determine user performance levels for different performance metrics.

instrument or camera. This can allow a surgeon to view anatomy from different perspectives without undocking the robot. Also, it may allow surgeons to operate throughout a larger workspace within the patient without undocking.

Motion pictures and movement parameters are recorded for both master controllers 36, 38 and too end effectors 26. The motion pictures may be recorded for 1) important surgical context information 2) for those who wish to visually study the surgery at a later time, but are not a source of the exact 3D positions of the instruments because videos are inherently 2D and are subject to geometric distortions of camera lenses. However, if left and right images from a 3D endoscope are recorded and camera calibration parameters are provided, then an accurate estimate of instrument location/pose in 3D may be determined.

The recorded kinematic data (e.g., position sensor data) on the other hand provides the exact 3D positions of the instruments.

TABLE 2

Master Workspace Range

| Input Controller - Left | Input Controller - Right |
|---|---|
| Definition: | Definition: |
| The volume in 3D within which the hand remains "most of the time" (e.g. the 3D volume of an ellipsoid | (same as L controller) Parameters: (same as L controller) |

TABLE I

Economy of Motion

| Tool/Arm 1 | Tool/Arm 2 | Tool/Arm 3 | Camera/Arm 4 | Input Controller - Left | Input Controller - Right |
|---|---|---|---|---|---|
| Definition: Total distance traveled by the end (tip) of the Tool/Arm Parameters: x, y, z positions of the end (tip) of this Tool/Arm | (same as Tool/Arm 1) Parameters: same | (same as Tool/Arm 1) Parameters: same | (same as Tool/Arm 1) Parameters: same | (same as Tool/Arm 1) Parameters: same | (same as Tool/Arm 1) Parameters: same |

Table 1 is an illustrative table structure including parameter values indicative of movement and/or actuation of corresponding input control components and tools that may be used to determine a user performance level for an economy of motion performance metric. In some embodiments, for example, input control movement and tool movement may be calculated from joint's angular orientation (or extension if it's a prismatic joint) and fixed mechanical dimensions of each mechanical linkage in every two consecutive joints. The economy of motion metric is determined based upon distances traveled by input control components and/or instruments. Tool/Arm 1 refers to a tool 26 coupled to a first one of the support arms/tool manipulators 72/73; tool/Arm 2 refers to a tool 26 coupled to a second one of the support arms/tool manipulators 72/73; and tool/Arm 3 refers to a tool 26 coupled to a third one of the support arms/tool manipulators 72/73. The camera/arm 4 refers to an imaging device coupled to a fourth one of the support arms/tool manipulators 72/73. It will be appreciated that a system 10 may include greater or fewer than four support arms/tool manipulators 72/73 and greater or fewer than four tools 26. An endoscopic camera may be inserted on any arm such that the arms do not necessarily have to have a static mapping to TABLE 2-continued Master Workspace Range centered on the centroid of hand's
x, y, z motion and envelopes the
hand's x, y, z position 85% of the time)
Parameters:
The x, y, z positions of the end (tip) of
this controller Table 2 is an illustrative table structure including parameter values indicative of movement of the right and left input controls 36, 38 that may be used to determine a value of a master workplace range performance metric, which is determined based upon volume of hand movements.

TABLE 3

Camera Movement Frequency/Efficiency (Shortest path), Duration

| Camera Movement Frequency | Camera Efficiency |
|---|---|
| Definition: number of times camera is moved per period of time Parameter components: system | Definition: absolute path length or ratio of path length to shortest path length from onset of camera |

TABLE 3-continued

Camera Movement Frequency/Efficiency (Shortest path), Duration

| | |
|---|---|
| log of camera control on/off events, follow on/off events, camera kinematic trace (x, y, z positions of camera tip) | movement to offset of camera movement Components: same as cam movement frequency |

Table 3 is an illustrative table structure including parameter values indicative of movement of a camera imaging device tool and actuation of a camera movement control that may be used to determine a value of a camera movement performance metric.

TABLE 4

Third Arm Swap Duration, Frequency

| | |
|---|---|
| Arm Swap Delay Definition: When surgeon switches controller from controlling Arm X to Arm Y (where X, Y can be 1, 2, 3), the delay is defined as the time delay between when the surgeons pushes the Arm-Swap Pedal and when he/she starts to move Arm Y. All delays made by the surgeon are recorded and may be aggregated (e.g. mean, median, standard deviation, etc are calculated) | Arm Swap Frequency Definition: the number of times a surgeon swaps control of instrument arms per unit time Parameters: Time of user's press of arm-swap per pedal, and task time. |

TABLE 4-continued

Third Arm Swap Duration, Frequency

Parameters:
Time of press of Arm-Swap
events, which are binary-
sensor on the arm-swap pedal
x, y, z position of the "swap-
to" arm (i.e. arm Y)

Table 4 is an illustrative table structure including parameter values indicative of movement of tool/Arm 1, tool/Arm 2, tool/Arm 3 and actuation of an Arm Swap components that may be used to determine a value of a third arm swap performance metric. A reason for arm swap capability is that at any moment a surgeon can engage at most two master controllers 36, 38 but there may be up to four instruments 26 inside the patient, and therefore the surgeon would need to change the association between a master controller and a slave instrument 26 during surgery. For example, when he/she activates the camera pedal, both hand controllers now control the zoom/pan/tilt of the endoscope camera. Similarly, for example, when he/she presses the third arm swap pedal, one of the two controllers 36, 38 is toggled between one of the two active non-camera instruments and a third non-camera instrument, hence 'third arm' swap. A third arm could be used to provide static retraction of tissue to expose relevant anatomy, for example.

TABLE 5

Idle Time - Period with No Activity at Control Console During Procedure

| Arm 1 | Arm 2 | Arm 3 | Camera/ Arm 4 | Input Controller - Left | Input Controller - Right | Head In | In following |
|---|---|---|---|---|---|---|---|
| Definition: Time during which Arm shows no detectable movement Parameters: The x, y, z position of this arm | (same as Arm 1) Parameters: | (same as Arm 1) Parameters: | (same as Arm 1) Parameters: | (same as Arm 1) Parameters: | (same as Arm 1) Parameters: | Definition: Time during which no head-in or head-out event are detected Parameters: Head-in sensor | Definition: Time during which no follow-on or follow-off event are detected Parameters: Head in sensor and grip sensors Head-in sensor |

Table 5 is an illustrative table structure including parameter values indicative of movement of tool/Arm 1, tool/Arm 2, tool/Arm 3 camera/Arm 4, right and left input controllers 36, 38, Head-In, and in following components that may be used to determine a value of idle time performance metric.

TABLE 6

Tool Speed

| Tool/Arm 1 | Tool/Arm 2 | Tool/Arm 3 | Input Controller - Left | Input Controller - Right |
|---|---|---|---|---|
| Definition: Speed metric includes the average speed and speed percentiles at an arbitrary set of percentiles (e.g. 50, 75, 90-percentile speeds are reported to describe the speeds that are faster than the end of the Tool/Arm e.g., 50%, | (Same as Tool/Arm 1) Parameters: | (Same as Tool/Arm 1) Parameters: | (Same as Tool/Arm 1) Parameters: | (Same as Tool/Arm 1) Parameters: |

TABLE 6-continued

Tool Speed

75%, 90% of the
time when the
Tool/Arm is not
idle.)
Parameters:
The x, y, z positions
of this Tool/Arm Table 6 is an illustrative table structure including parameter values indicative of movement of tool/Arm 1, tool/Arm 2, tool/Arm 3 and right and left input controllers 36, 38 that may be used to determine a tool speed performance metric.

TABLE 7

Wrist Manipulation

| Tool/Arm 1 | Tool/Arm 2 | Tool/Arm 3 | Input Controller - Left | Input Controller - Right |
|---|---|---|---|---|
| Definition: Total absolute rotation movement of the instrument wrist along the: wrist roll axis wrist pitch axis wrist yaw axis Parameters: The angular positions of all available wrist joints of this instrument | (Same as Tool/Arm 1) Parameters: | (Same as Tool/Arm 1) Parameters: | (Same as Tool/Arm 1) Parameters: | (Same as Tool/Arm 1) Parameters: |

Table 7 is an illustrative table structure including parameter values indicative of movement of tool/Arm 1, tool/Arm 2, tool/Arm 3 and right and left input controllers 36, 38 that may be used to determine a wrist performance metric. It will be appreciated that the ability to use wrists is an advantage of robotic-assisted surgery over laparoscopic surgery, where instruments do not have wrists, because wrists allows for much more intricacy in manipulations. Robot-assisted surgeons are encouraged to fully utilize instrument wrists in surgical steps where intricate articulation is involved (such as suturing). It is believed that wrist use per time interval may increase as a robot-assisted surgeon gains fluency with manipulating tools 26 of the system 10.

Tables 1-7 show example performance metrics determined based upon one or more parameter values, each indicative of a measure of a type of movement of one or more different components of the system 10. Referring to Table 1, for example, a first metric, i.e. a metric for economy of motion, may be determined based upon six different parameter values for tool/Arm 1, tool/Arm 2, tool/Arm 3 camera/Arm 4, and right and left input controllers 36, 38. Alternatively, for example, a value for the first metric may be determined based upon parameter values for a subset of the six components, such as based upon parameter values only for tool/Arm 1 alone, or based upon parameter values for only tool/Arm 1 and the right and left input controls 36, 38.

Example Procedures and Tasks

A user's performance level for a performance metrics according to the parameters of Tables 1-7 may be determined based upon performance level for a single procedure, multiple procedures or from single or multiple steps/tasks or sub-tasks/gestures within one or more procedures or steps of procedures. These metrics also may be computed over sliding windows of arbitrary length that are agnostic of the task but can still be used to estimate surgeon efficiency/skill/performance. Procedures and tasks used to determine a user's performance level may be selected based upon the effectiveness of the procedure in differentiating among different skill levels. Once a surgeon-in-training's performance level is determined, appropriate training exercises may be selected to improve the surgeon's performance level to move it up from resident skill level to a fellow skill level or from fellow skill level to an attending skill level or to just practice to maintain or to further improve upon a current skill level.

Figure 7A:
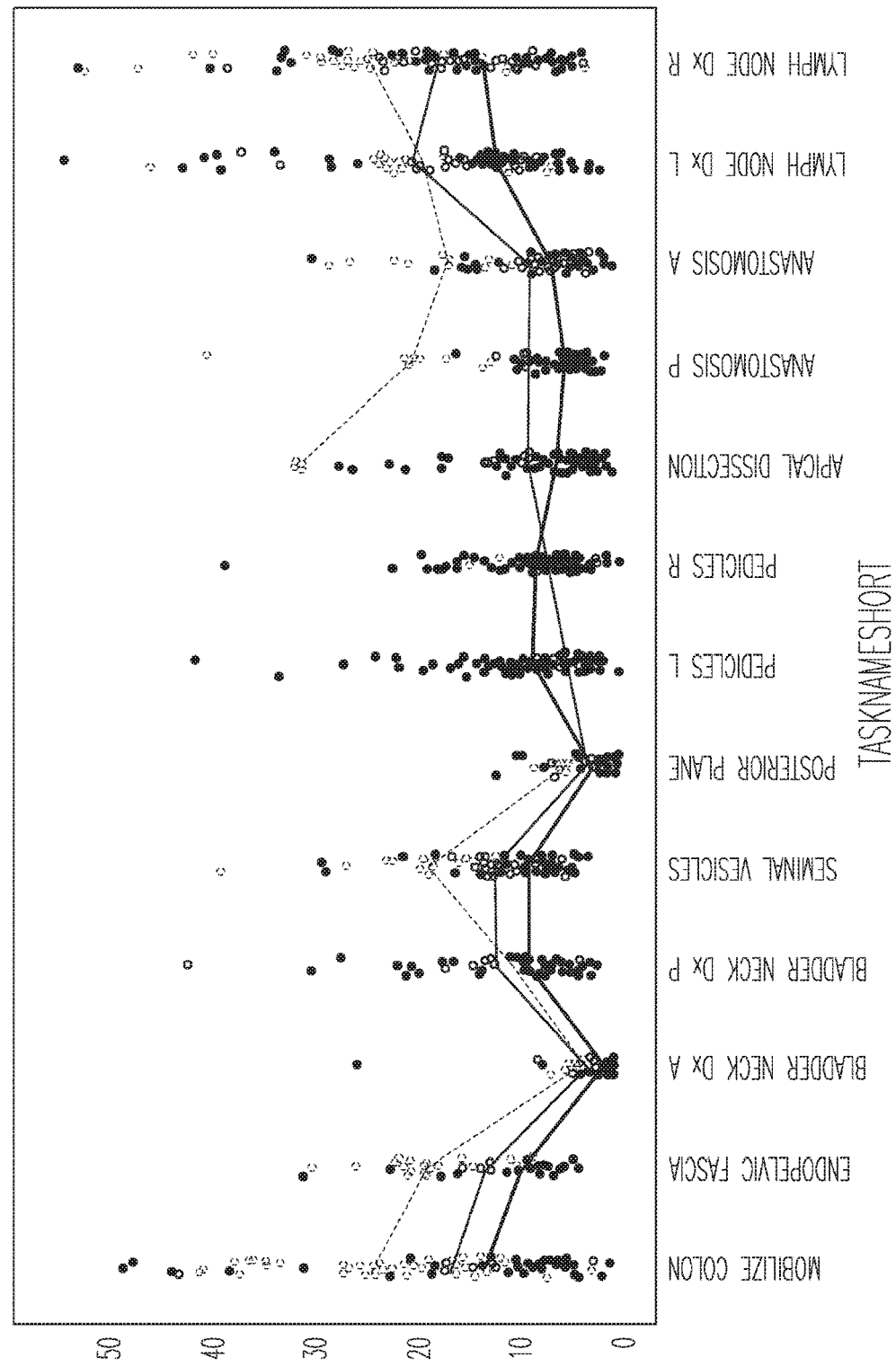
FIG. 7A is an illustrative drawing showing a comparative first skill level chart for example tasks performed during an example first clinical procedure.

FIG. 7A is an illustrative drawing showing a first comparative skill level chart with comparative performance levels for users from three different clinical skill levels measured according to the total duration (time) metric, for example tasks performed during an example first clinical procedure. The example skill levels are clinical skill levels are those of an attending, a fellow and a resident. An attending surgeon typically has the highest skill level. A resident surgeon typically has the lowest. A fellow's skill level typically falls between that of attending and resident. The example first clinical procedure, robot-assisted Prostatectomy, includes multiple tasks/steps indicated on the x-axis of the figure.

Figure 7B:
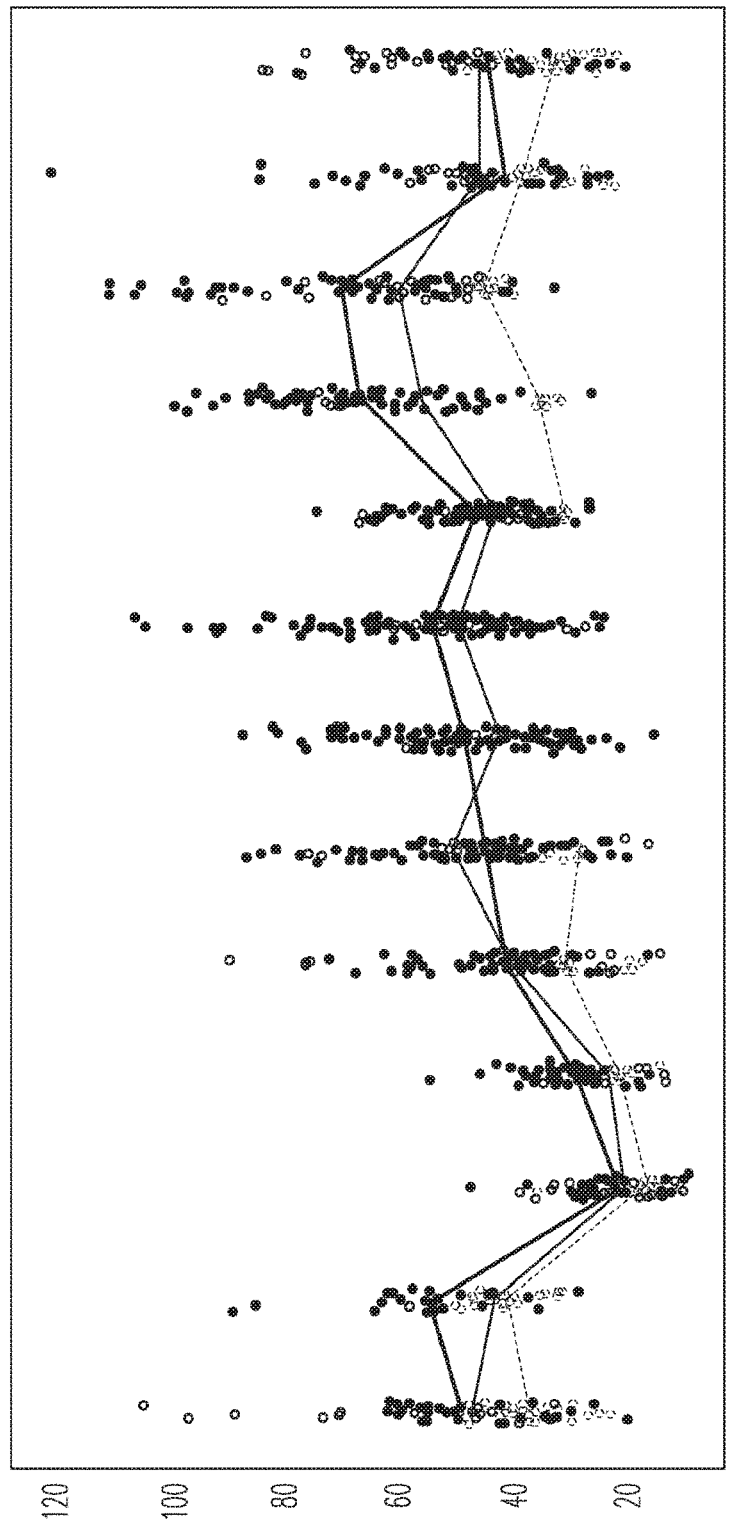
FIG. 7B is an illustrative drawing showing a second comparative skill level chart for example tasks performed during an example second clinical procedure.

FIG. 7B is an illustrative drawing showing a second comparative skill level chart with comparative performance levels for users from three different clinical skill levels measured according to a wrist manipulation metric, for example tasks performed during an example second clinical procedure. The example second clinical procedure, robot-assisted Prostatectomy, includes multiple tasks.

Figure 7C:
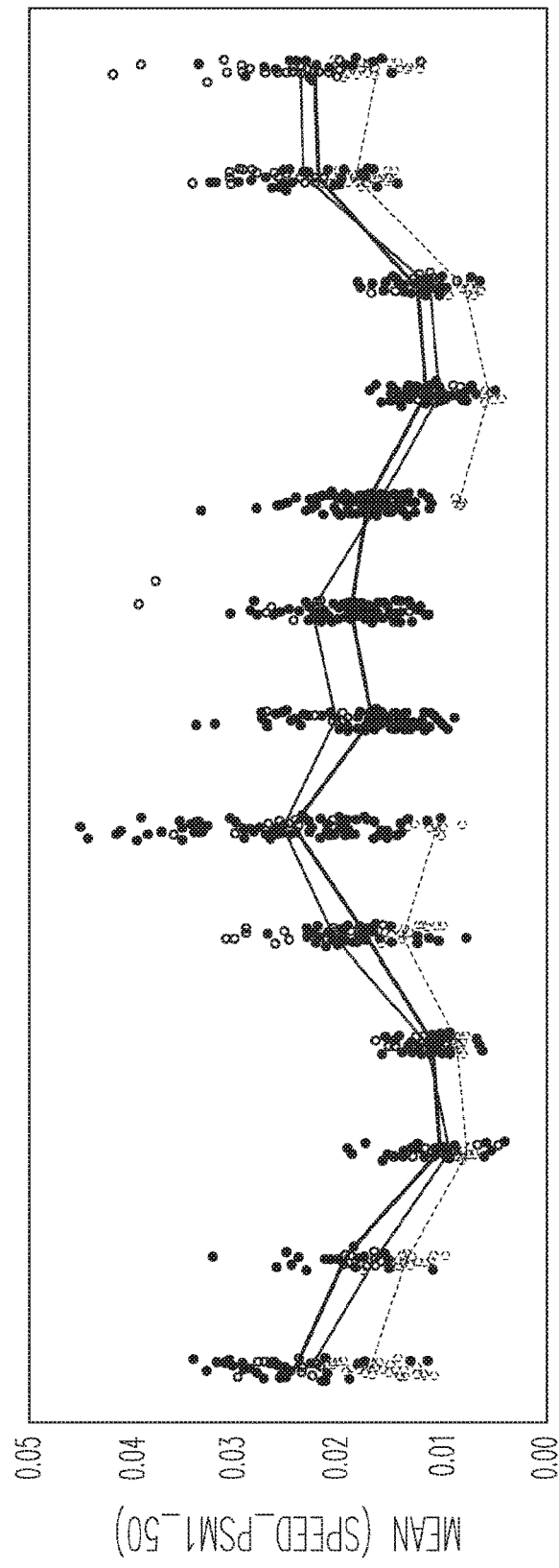
FIG. 7C is an illustrative drawing showing a third comparative skill level chart for example tasks performed during an example third clinical procedure.

FIG. 7C is an illustrative drawing showing a third comparative skill level chart with comparative performance levels for users from three different clinical skill levels measured according to a (mean) tool speed metric, for example tasks performed during an example third clinical procedure. The example third clinical procedure, robot-assisted Prostatectomy, includes multiple tasks.

The first skill level charts of FIGS. 7A-7C shows that differences in performance levels as measured using the first metric for users with different skill levels are greater for some tasks than for others. User performance levels for different metrics may be determined based upon user performance of entire procedures or based upon user performance of individual tasks within a procedure or based upon combinations of tasks within a procedure. User performance levels may be used to rank user performance during user training. Certain procedures, tasks or combinations of task may be better differentiators of user performance levels than others for certain metrics. For example, for the first and second procedures represented by FIGS. 7A-7B, differences in user performance levels for users with different skill levels as measured by the duration and wrist manipulation metrics for the task named 'Anastomosis P' within the first and second procedures are greater than differences in user performance levels for users with different skill levels as measured by the first metric for the task named 'Bladder Neck Dx A'. However, the task named 'Anastomosis P' within the third procedure is not such a good differentiator for the tool speed metric. Thus, some procedures and some tasks are more effective than others for determining comparative user skill levels based upon a particular metric. Specifically, for example, user's performance of the Anastomosis P task according to the first metric is better differentiator of a user's skill level than is the user's performance of the Bladder Neck Dx A task according to the economy of motion metric. Conversely, some tasks are more effective than others for training users to improve their skill level as measured by a particular metric. Specifically, for example, user practice at the Anastomosis P task is more likely to improve a user's skill level as measured by the economy of motion metric is user practice at the Bladder Neck Dx A task.

Indexing Motion Pictures Based Upon User Metrics

Figure 8:
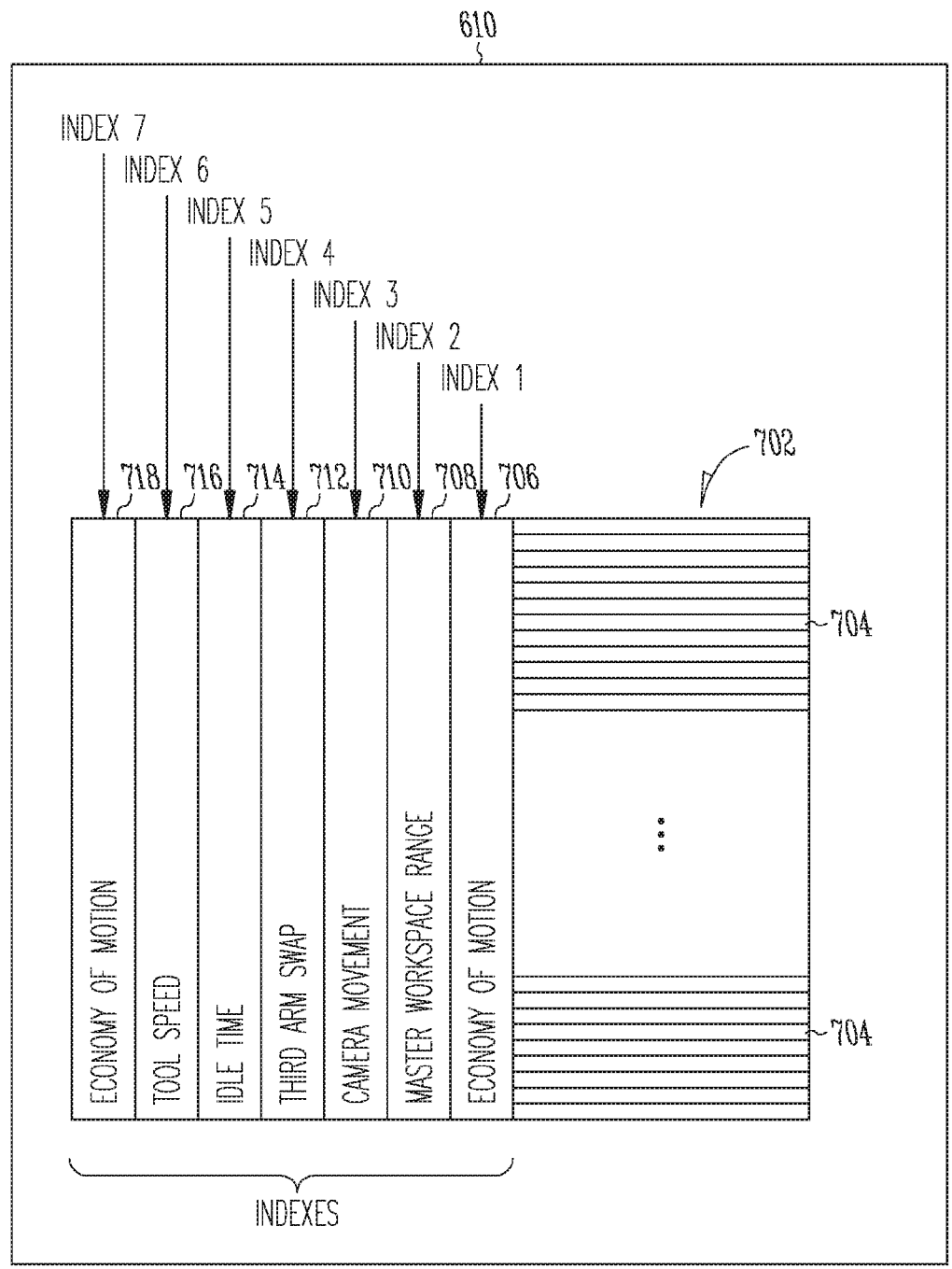
FIG. 8 is an illustrative drawing representing a collection of motion pictures and a multiple index structures to index the collection of motion pictures based upon user performance levels for multiple performance metrics.

FIG. 8 is an illustrative drawing representing a collection 702 of motion pictures 704 and multiple index structures to index the collection of motion pictures based upon user performance for multiple metrics. A plurality of users may provide manual input to one or more input control components 36, 37, 38, 47 of the system 10 to control one or more tools 26/28 in the performance of one or more tasks of one or more procedures. An imaging device 28 may capture motion picture images of movement of tools 26/28 during performance of the one or more tasks under user control. In some embodiments, a purpose of video recording is to capture the entire surgical scene including the instruments so that, for example, a human observer (or computer algorithm) can evaluate the interaction between the surgeon/instruments and the surgical scene from the videos at a later time. Sensors 36S, 37S, 38S, 47S may sense actuation of input control components 36, 37, 38, 47 and/or changes in position and/or orientation of input control components 36, 37, 38, 47 and/or tools 26/28 during performance of the one or more tasks by the users. User performance for multiple metrics may be determined based upon the users' manual input to one or more input control components 36, 37, 38, 47 and corresponding movement of the one or more tools 26/28.

More particularly, the electronics system 24 may be configured to produce a first index 706 that indexes motion pictures 704 of the collection 702 based upon economy of motion metric values determined for users controlling movement of one or more tools 26/28 shown in corresponding motion pictures, or other surgeon interaction with the system 10, such as actuating a button to effect a configuration change, for example. The electronics system 24 may be configured to produce a second index 708 that indexes motion pictures 704 of the collection 702 based upon master workspace range metric values determined for users controlling movement of one or more tools 26/28 shown in corresponding motion pictures. The electronics system 24 may be configured to produce a third index 710 that indexes motion pictures 704 of the collection 702 based upon camera movement metric values determined for users controlling movement of one or more tools 26/28 shown in corresponding motion pictures. The electronics system 24 may be configured to produce a fourth index 712 that indexes motion pictures 704 of the collection 702 based upon third arm swap metric values determined for users controlling movement of one or more tools 26/28 shown in corresponding motion pictures. The electronics system 24 may be configured to produce a fifth index 714 that indexes motion pictures 704 of the collection 702 based upon idle time metric values determined for users controlling movement of one or more tools 26/28 shown in corresponding motion pictures. The electronics system 24 may be configured to produce a sixth index 716 that indexes motion pictures 704 of the collection 702 based upon tool speed metric values determined for users controlling movement of one or more tools 26/28 shown in corresponding motion pictures. The electronics system 24 may be configured to produce a seventh index 718 that indexes motion pictures 704 of the collection 702 based upon a wrist movement economy of motion metric values determined for users controlling movement of one or more tools 26/28 shown in corresponding motion pictures. The electronics system 24 may be configured to produce many more indices that index motion pictures 704 of the collection 702 based on metrics derived from users controlling the system.

Determining User Performance Levels Based on Metrics

A user's metric is used to index to the collection of motion pictures 702, a motion picture showing that user's control of movement of tools 26/28. The user's performance score may depend upon multiple metrics such as but not limited to those listed in Table 1 through 7. Moreover, a user may have multiple performance scores for multiple different surgical settings or applications.

Machine Learning (ML) may be employed to determine a user performance score based upon values of one or many of the user's metrics. In some embodiments, a high performance score is defined as "performing like known expert surgeons." In alternative embodiments, alternative performance scores may be determined based on more goal-specific outcomes, e.g. "leading to least post-operative recovery time" or "leading to least post-operative complication rate." The user performance scores may be used to index motion pictures based upon user performance level, that portray movement of one or more components controlled by the different users during performance of the surgical or diagnostic procedure. More particularly, an electronics system 24 may be configured to perform an ML process to train an ML model to produce a performance level score for a metric of user performance based upon values of one or more parameters representing user-imparted movement of one or more input control components and/or tools.

For example, multiple attending skill-level surgeons and multiple resident skill-level surgeons may perform a clinical procedure, such as the robot-assisted Prostatectomy clinical procedure of FIG. 7A, which includes multiple tasks. During each surgeon's performance of the one or more tasks of the clinical procedure, the surgeon provides manual input to one or both of the right and left control inputs 36, 38 that control movement of one or more tools 26/28. A processor causes a machine-readable storage device to record values of movement parameters for one or more components that are actuated or that move in response to the surgeon's input to control input components 36, 38. Furthermore, during each surgeon's performance, an image capture tool 28 captures a motion picture of the surgical setting showing movement of one or more of Arm 1, Arm 2, Arm 3 in response to manual input provided by the surgeon at the right and left control inputs 36, 38. The surgeon may change position of the image capture tool 28 during performance of the procedure, which in turn, changes the perspective from which the surgical scene and Arms 1, 2, or 3 are viewed by the surgeon. In some embodiments, changes in viewing perspective due to camera movement also may be visible in the recorded motion pictures.

In some embodiments, the ML model includes a support vector machine (SVM) model. In some embodiments, supervised learning is used to train an SVM model. Training information to train an SVM model may be generated based upon performance of clinical procedures or clinical tasks by attending-skill-level surgeons and resident-skill-level surgeons. More specifically, continuing with the example robot-assisted Prostatectomy clinical procedure of FIG. 7A, during ML model training, a performance vector may be produced for each surgeon's performance of the clinical procedure. A surgeon's performance vector indicates parameter values recorded during the surgeon's performance, that represent movement of one or more of Arm 1, Arm 2, Arm 3, Camera, Master Controller Left and Master Controller Right, in response to manual input received from the surgeon. To train an SVM model, performance vectors produced for attending-skill-level surgeons are labeled 'expert' and performance vectors produced for resident-skill-level surgeons are labeled as 'novice'.

The SVM ML training process develops a hyperplane or a set of hyperplanes to classify user performance data. Each user's performance may be represented as a p-dimensional vector representing 'p' metric values, in which each metric value is derived from the movement or state of one or more components in response to manual input by the user during performance of one or more tasks of a clinical procedure. In some embodiments, the training process identifies a hyperplane or a set of hyperplanes that provide the widest separation, or margin, between two classes, i.e. between expert and novice. Once the SVM model has been trained, it may be used to classify a new user's performance level based upon metric values obtained from component values recorded during that user's performance of one or more tasks of a clinical procedure. A distance between a new user's performance vector and an SVM's hyperplane or set of hyperplanes is indicative of a user's performance level. Thus, an SVM model may be used to produce an overall performance score for a new user based upon distance of the new user's performance parameter vector from an SVM's hyperplane or set of hyperplanes.

An SVM separates expert and novice users on two different sides of a hyperplane in the "high-dimensional feature space," i.e. the hyperplane acts as a decision boundary: If a new user is on the EXPERT side of the hyperplane, he/she is more like an EXPERT. The further from the boundary he/she is, the more EXPERIENCED he/she is. If a new user is on the NOVICE side of the hyperplane, he/she is more like a NOVICE. The further he/she is from the boundary, the more INEXPERIENCED he/she is. This distance is used as the raw performance score. A raw score of 0, i.e. user is sitting on the "fence" aka the decision boundary aka the hyperplane, means the model considers that user to be ambiguous. Raw score >0 means user is more like an expert, and <0 means user is more like a novice. A raw score between −2 to +2, for example, can be scaled to a final performance score of 65 to 100. (The extremes, i.e. −2 and +2, can be chosen based on the sample population at hand in order to "curve the grade" to a desired range.)

It will be appreciated that different SVM models can be produced for different sets of metrics, such as for economy of motion and/or master workspace range and/or camera movement and/or third arm swap, and so on, based upon different tasks or combinations of tasks. Moreover, it will be appreciated that an SVM model may be represented as a formulation used to compute a performance level score based upon a weighted sum of metric values.

An illustrative example LINEAR SVM model may be represented as indicated in the following Table 8:

TABLE 8

Example SVM ML model raw score = (−0.15322146)*MeanCameraMoveDuration + 0.17751776*CameraMoveEfficency + (−0.10438462)*(EconomyOfMotion_Arm1 + EconomyOfMotion_Arm2) + 0.31648808*(Speed75Percentile_Arm1 − Speed25Percentile_Arm1) + 0.27260756*(WristTotalRotationPerMin_Arm1 + WristTotalRotationPerMin_Arm2) + 0.13112593*ThirdArmSwapsPerMin The coefficients in the above formulation were generated by the SVM after it had "learned" or "got trained" on data. It is noted that non-linear SVMs are more powerful and flexible than linear SVMs, but the score cannot longer be written as weighted sum, and requires more complex non-linear functions.

Some alternative machine learning scoring/classification methods include logistic regression, stepwise logistic regression, ensemble of decision trees, naïve bayes classifier, hybrids of these with majority vote wins. Any classification algorithm can be used: for classification algorithms that yield a decision boundary (e.g. SVM), the above distance-to-boundary method can be used to generate a performance score; for classification algorithms that yield probabilities (e.g. logistic regression, stepwise logistic regression, any decision tree model such as random forest, naïve Bayes, etc.), higher probabilities of being an expert can be interpreted as high-performance scores, and vice versa. Any combination of more than one classification algorithms can also be used (performance score is the weighted sum of scores generated by all algorithms)

Comparative Performance Meter UI

Figure 9:
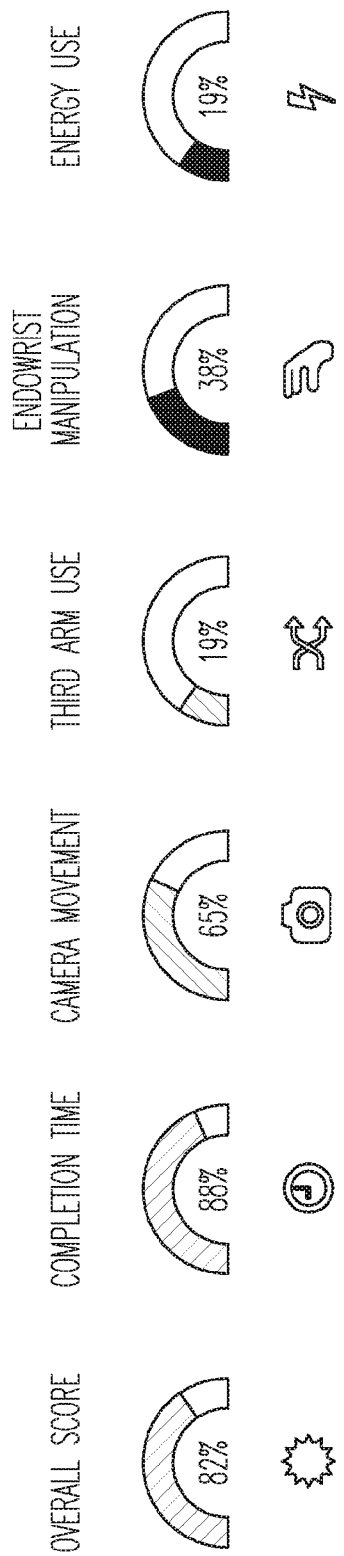
FIG. 9 is illustrative drawings showing example computer generated comparative performance user interface (UI) meters displayed on a computer display.

FIG. 9 is illustrative drawings showing example computer generated comparative performance user interface (UI)

meters displayed on a computer display screen indicating user's comparative ranking according to different metrics. The user interface may be displayed on a display screen such as a computer screen or a handheld device display screen, for example. In some embodiments, the comparative performance meters indicate a user's performance in comparison to the performance of other users. The illustrative meters of FIG. 9 indicate a user's performance for a different skill level metric for a single example task referred to as 'whole organ excision'. A first meter that indicates a user's performance level for an overall score, such as one derived from the methods in Table 8 that combines many metrics. In general, a higher overall score is more proficient. The example first meter shows that the user has an 82nd percent proficiency level for an overall metric. The second meter that indicates a user's performance for a completion time metric. In general, a shorter completion time is more efficient. The example second meter shows that the user has an 88th percent proficiency level for the completion time metric. A third meter indicates a user's performance for a camera movement metric. In general, shorter duration camera movement is more efficient. The example third meter shows that the user has a 65th percent proficiency level for the camera movement metric. A fourth meter indicates a user's performance for a third arm use metric. In general, more frequent third arm swaps is more efficient. The example fourth meter shows that the user has a 19th percent proficiency level for the third arm use metric. A fifth meter indicates a user's performance for a wrist manipulation metric. In general, a frequency larger overall wrist manipulation movement is more efficient. The example fifth meter shows that the user has a 38th percent proficiency for the third arm average delay metric. A sixth meter indicates a user's performance for energy use. In general, a frequency lower frequency of energy use is more efficient. The example sixth meter shows that the user has a 19th percent proficiency level for the master clutch frequency metric. These proficiency levels can be any engineered scoring system, rank orderings among peer surgeons, percentile rankings, etc.

Metric-Based Motion Picture Selection UI

Figure 10A:
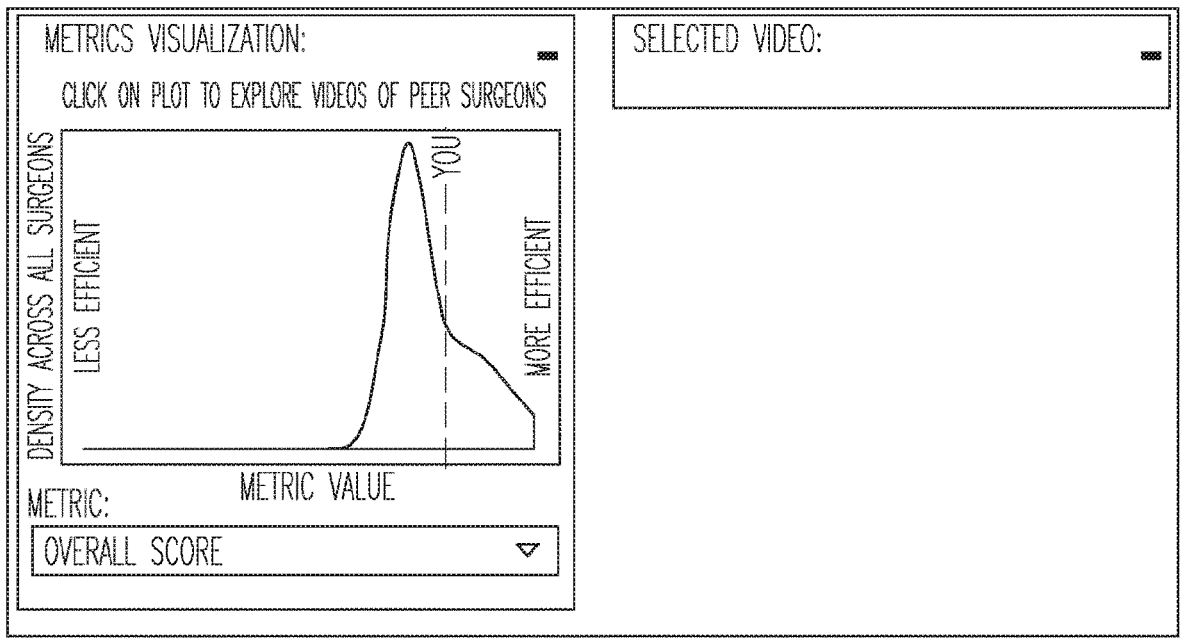
FIGS. 10A-10B are illustrative first performance metric-based motion picture selection user interface displays providing a first interactive visual index to select among a collection of motion pictures based upon an overall performance metric.
Figure 10B:
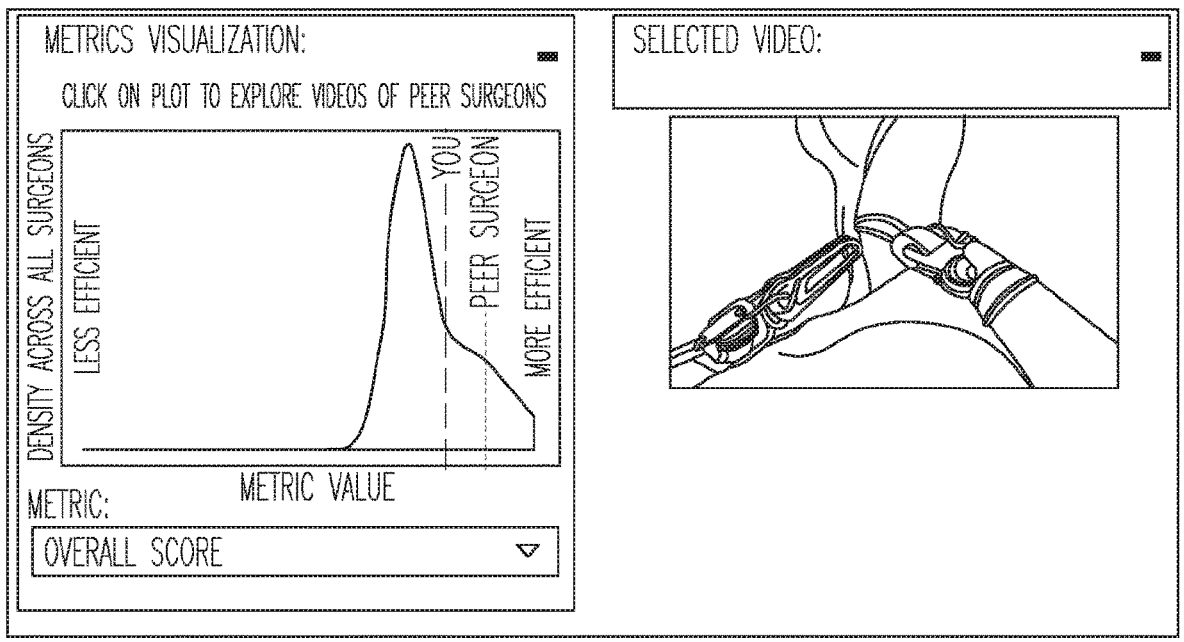

FIGS. 10A-10B are illustrative first metric-based motion picture selection user interface displays providing a first interactive visual index to select among a collection of motion pictures based upon an overall metric. The overall performance metric represents an overall score based on a combination of individual metrics. In some embodiments, a larger overall score is better. The first metric-based motion picture selection user interface displays may be provided at the viewer display 31 of the control console 16 and/or at the separate display screen 60. A user uses a pull-down menu to select the first metric-based motion picture selection user interface. It will be appreciated that an overall score is not based on any specific one of Tables 1-7, for example, since the score is the SVM's output (raw score), scaled to a display ranking in a more familiar range (e.g. between 65 and 100). The SVM, in turn, is based on a subset (potentially all) of the parameters in Tables 1-7. Different respective motion pictures from the collection may portray movement of one or more end effectors controlled by different respective users during performance of a surgical or diagnostic task. The motion pictures may be stored in the machine-readable storage device 609. The motion pictures of the collection stored within the storage device are indexed based upon the first metric, also referred to herein as an overall metric. More specifically, respective values may be determined for one or more parameters for each respective motion pictures of the collection. It will be appreciated that each respective overall metric value is indicative of a respective performance level of a respective user providing user input to a manual control component 36, 37, 38, 47 to control movement of the at least one tool 26/28 portrayed in a corresponding respective motion picture.

The overall metric-based motion picture selection user interface of FIGS. 10A-10B includes a first histogram curve in which a vertical axis represents across all users, who may be surgeons, and a horizontal axis represents overall performance level. Increasing values on the vertical axis indicate a greater density of users at a corresponding performance level for the overall metric. Increasing metric values on the horizontal axis may indicate an overall performance level having grater efficiency or lesser efficiency, depending on the particular metric (e.g., higher camera movement frequency is good but higher completion is bad). A user may refer to the first meter of the comparative performance user interface of FIG. 9 to determine his or her personal value for the overall metric. The user's personal overall metric value corresponds to a horizontal axis coordinate of the histogram, which indicates a density of users at that value for the first metric. The first histogram provides a visual indication of a user's personal value relative to the values for the first metric of other users. A user may thereby determine how his or her performance as measured by the first metric compares with other users.

Referring to FIG. 10B, there is shown an illustrative drawing showing a display of the first interactive visual index that includes a selection indicator indicating a user's selection of an indexed overall metric value on the index and also showing a display of a motion picture from the collection of motion pictures, corresponding to the selected overall metric value. In accordance with some embodiments, a user may interact with the overall metric-based motion picture selection user interface to select a motion picture from the collection by pointing to a location on the first histogram curve using a cursor, stylus, finger or other pointing device, for example. Different horizontal curve coordinates of the first histogram correspond to different values of the overall metric, and the motion picture collection is indexed according to overall metric values. In response to a user selecting a horizontal coordinate of the first histogram that corresponds to a value of the first metric, a computer system causes display of a motion picture from the collection that is indexed to the selected overall metric value and also causes display of the selection indicator at a location of the first histogram curve indicating the selected value for the overall metric. Thus, a user may use the comparative performance user interface of FIG. 9 to determine his or her performance level as measured by the overall metric, may use the first interactive visual index of the first metric-based motion picture selection user interface of FIG. 10A to select a value for the overall metric. In response to the user's selection, a motion picture is displayed depicting movement of one or more end effectors by a user having a performance level for the overall metric represented by the selected overall metric value. It will be appreciated that a user may select a value for the overall metric that represents a skill level that is superior to, inferior to, or at the same level as his or her own skill level. The user may watch the selected video to learn from other users by observing movement of one or more tools 26/28 under their control.

Figure 11A:
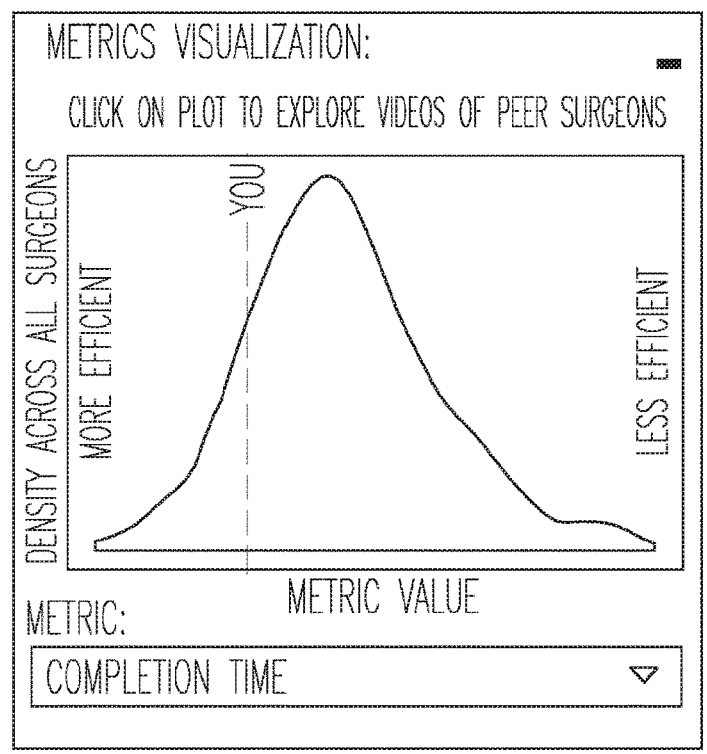
FIGS. 11A-11B are illustrative second performance metric-based motion picture selection user interface displays providing a second interactive visual index to select among a collection of motion pictures based upon a completion time metric.
Figure 11B:
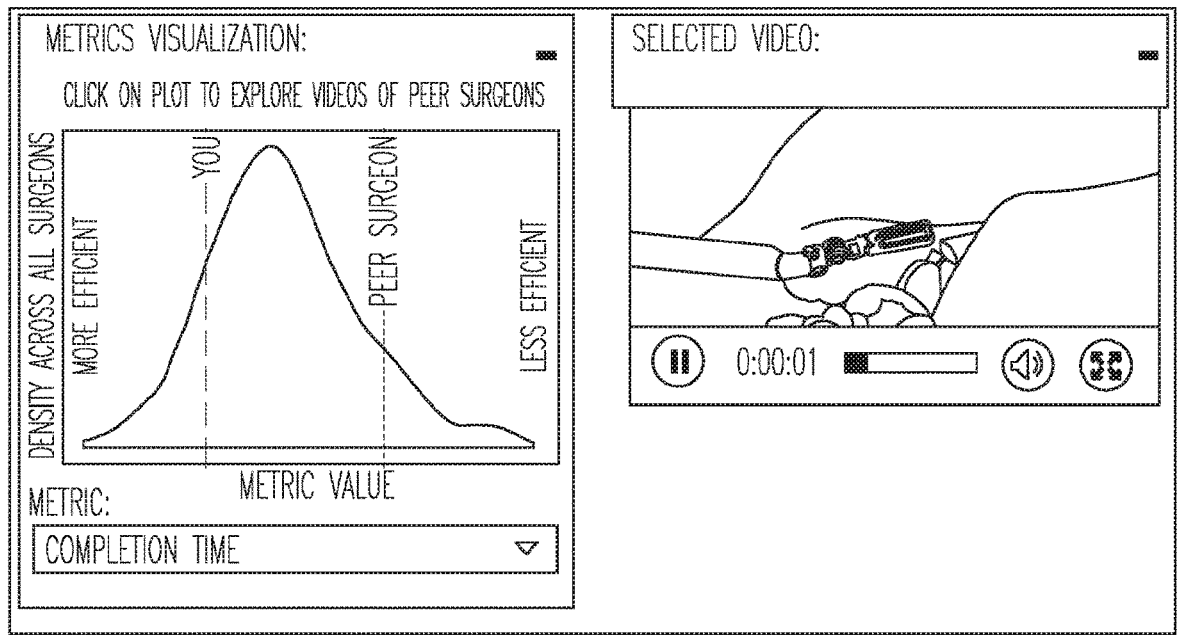

FIGS. 11A-11B are illustrative second metric-based motion picture selection user interface displays providing a second interactive visual index to select among a collection of motion pictures based upon a completion time metric. A user may use a pull-down menu to select the second metric-based motion picture selection user interface. The completion time metric represents a total time to complete a task. Shorter completion time is more efficient. The motion pictures of the collection stored within the storage device 609 are additionally indexed based upon the second metric, also referred to herein as a completion time metric. More specifically, respective values may be determined for one or more parameters for each respective motion pictures of the collection that are indicative of completion time. The completion time metric-based motion picture selection user interface of FIGS. 11A-11B includes a second histogram curve in which a vertical axis represents density of users across all users, who may be surgeons, and a horizontal axis represents completion time. Increasing values on the vertical axis indicate a greater density of users at a corresponding performance level for the completion time metric. Increasing metric values on the horizontal axis indicate longer completion time, which is less efficient. A user who is more skilled according to the completion time metric has a shorter completion time. A user may refer to the second meter of the comparative performance user interface of FIG. 9 to determine his or her personal value for the completion time metric. The second histogram provides a visual indication of a user's personal value relative to the values for the second metric of other users. A user may thereby determine how his or her performance as measured by the second metric compares with other users. Referring to FIG. 11B, there is shown an illustrative drawing showing a display of the second interactive visual index that includes a selection indicator indicating a user's selection of an indexed completion time metric value on the index and also showing a display of a motion picture from the collection of motion pictures, corresponding to the selected completion time metric value. Further details of user selection based upon the second interactive visual index will be understood from the discussion above.

Figure 12A:
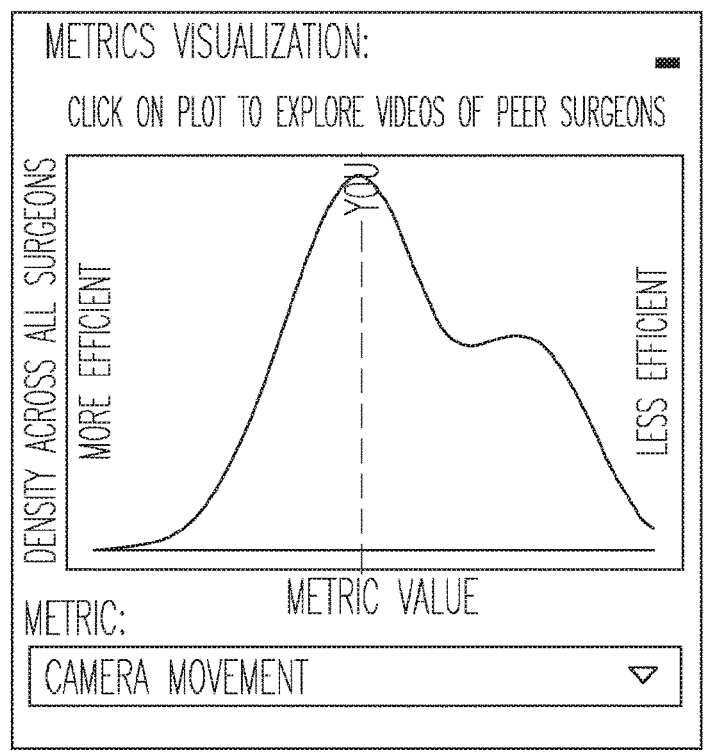
FIGS. 12A-12B are illustrative third performance metric-based motion picture selection user interface displays providing a third interactive visual index to select among a collection of motion pictures based upon a camera movement metric.
Figure 12B:
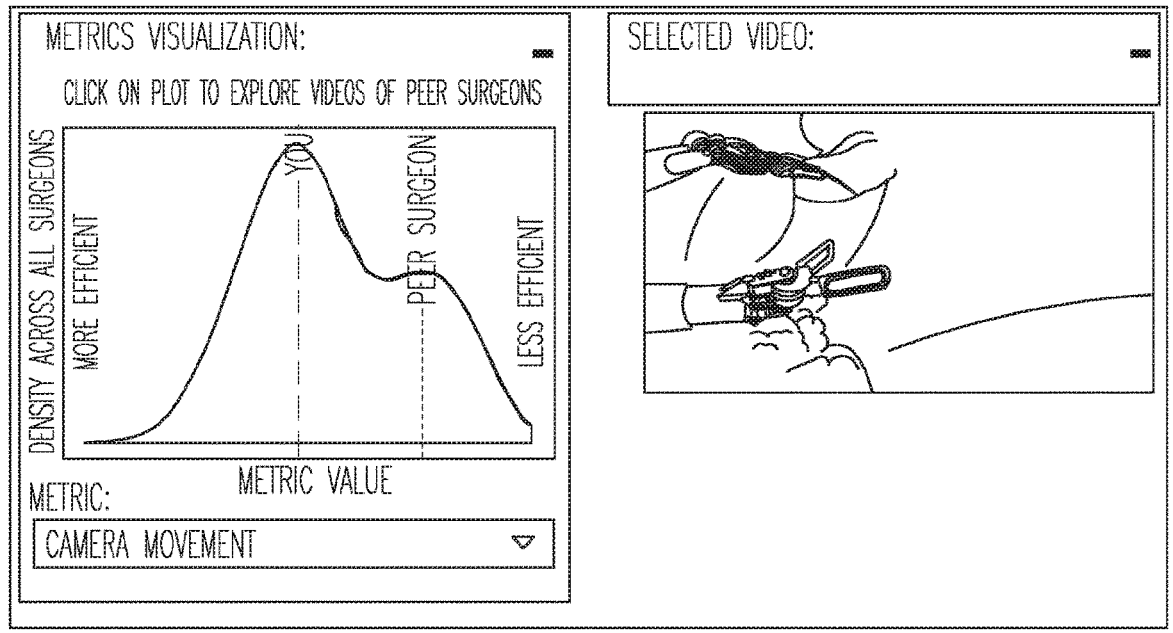

FIGS. 12A-12B are illustrative third metric-based motion picture selection user interface displays providing a third interactive visual index to select among a collection of motion pictures based upon a camera movement metric. A user may use a pull-down menu to select the third metric-based motion picture selection user interface. The camera movement metric represents a mean duration of camera movements. Shorter duration is more efficient. The motion pictures of the collection stored within the storage device 609 are additionally indexed based upon the third metric, also referred to herein as a camera movement metric. More specifically, respective values may be determined for one or more parameters for each respective motion pictures of the collection. Respective camera movement metric values for the respective motion pictures of the collection may be determined based upon corresponding respective values of the one or more parameters from Table 3. The camera time metric-based motion picture selection user interface of FIGS. 12A-12B includes a third histogram curve in which a vertical axis represents density of users across all users, who may be surgeons, and a horizontal axis represents duration of camera movements. Increasing values on the vertical axis indicate a greater density of users at a corresponding performance level for the overall metric. Increasing metric values on the horizontal axis indicate longer duration of camera movements, which is less efficient. In some embodiments, increasing metric values on the horizontal axis indicate frequency of movement or efficiency of movement, for example. A user who is more skilled according to the camera movement metric has a shorter camera movement time. A user may refer to the third meter of the comparative performance user interface of FIG. 9 to determine his or her personal value for the camera movement metric. The third histogram provides a visual indication of a user's personal value relative to the values for the third metric of other users. A user may thereby determine how his or her performance as measured by the third metric compares with other users. Referring to FIG. 12B, there is shown an illustrative drawing showing a display of the third interactive visual index that includes a selection indicator indicating a user's selection of an indexed camera movement metric value on the index and also showing a display of a motion picture from the collection of motion pictures, corresponding to the selected camera movement metric value. Further details of user selection based upon the third interactive visual index will be understood from the discussion above.

Figure 13A:
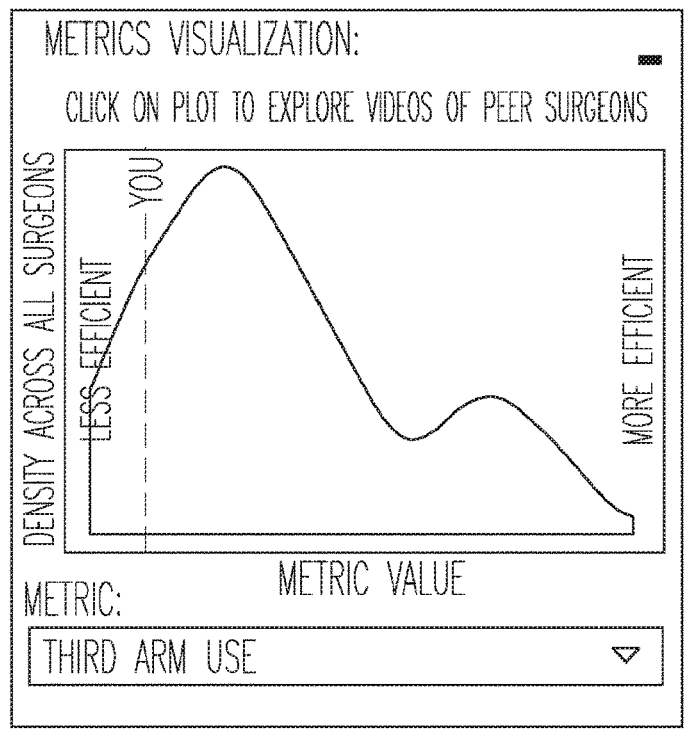
FIG. 13A-13B are illustrative fourth performance metric-based motion picture selection user interface displays providing a fourth interactive visual index to select among a collection of motion pictures based upon a third arm use metric.
Figure 13B:
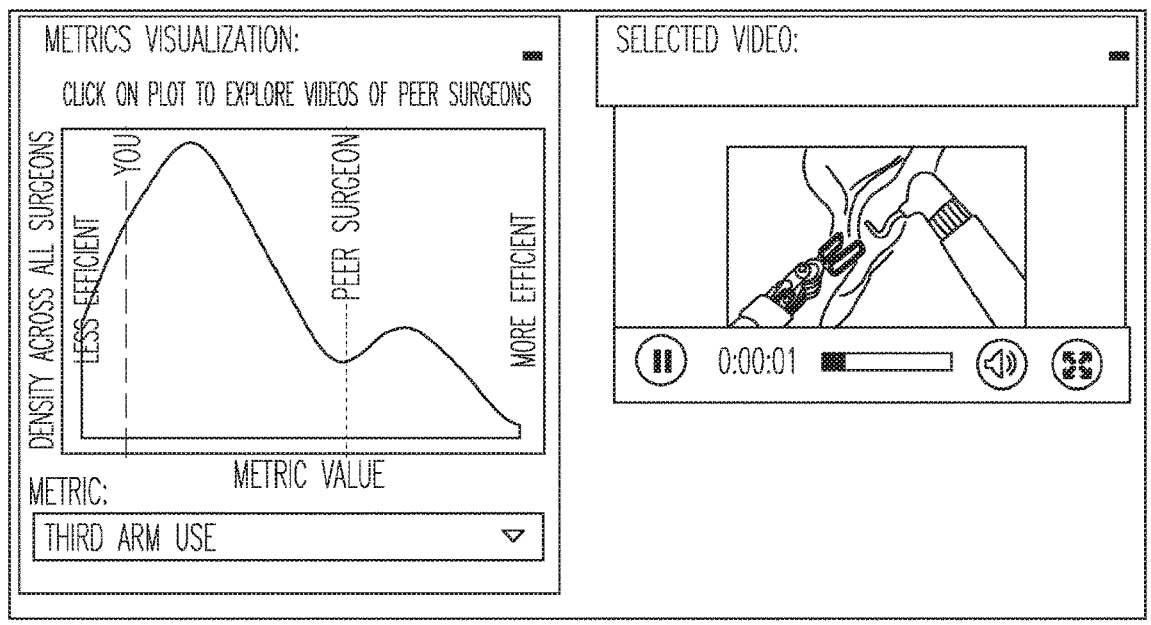

FIG. 13A-13B are illustrative fourth metric-based motion picture selection user interface displays providing a fourth interactive visual index to select among a collection of motion pictures based upon a third arm use metric. A user may use a pull-down menu to select the fourth metric-based motion picture selection user interface. The third arm use metric represents a frequency of third arm swaps. More frequent swaps is more efficient. The motion pictures of the collection stored within the storage device 609 are additionally indexed based upon the fourth metric, also referred to herein as a third arm swap metric. More specifically, respective values may be determined for one or more parameters for each respective motion pictures of the collection. Respective third arm swap metric values for the respective motion pictures of the collection may be determined based upon corresponding respective values of the one or more parameters from Table 4. The third arm swap metric-based motion picture selection user interface of FIGS. 13A-13B includes a fourth histogram curve in which a vertical axis represents density of users across all users, who may be surgeons, and a horizontal axis represents frequency of third arm movements. Increasing values on the vertical axis indicate a greater density of users at a corresponding performance level for the overall metric. Increasing metric values on the horizontal axis indicate greater frequency of third arm swaps, which is more efficient. A user who is more skilled according to the third arm swap metric has more frequent third arm swaps. A user may refer to the fourth meter of the comparative performance user interface of FIG. 9 to determine his or her personal value for the third arm swap metric. The fourth histogram provides a visual indication of a user's personal value relative to the values for the fourth metric of other users. A user may thereby determine how his or her performance as measured by the fourth metric compares with other users. Referring to FIG. 13B, there is shown an illustrative drawing showing a display of the fourth interactive visual index that includes a selection indicator indicating a user's selection of an indexed third arm swap metric value on the index and also showing a display of a motion picture from the collection of motion pictures, corresponding to the selected third arm swap value. Further details of user selection based upon the fourth interactive visual index will be understood from the discussion above.

Figure 14A:
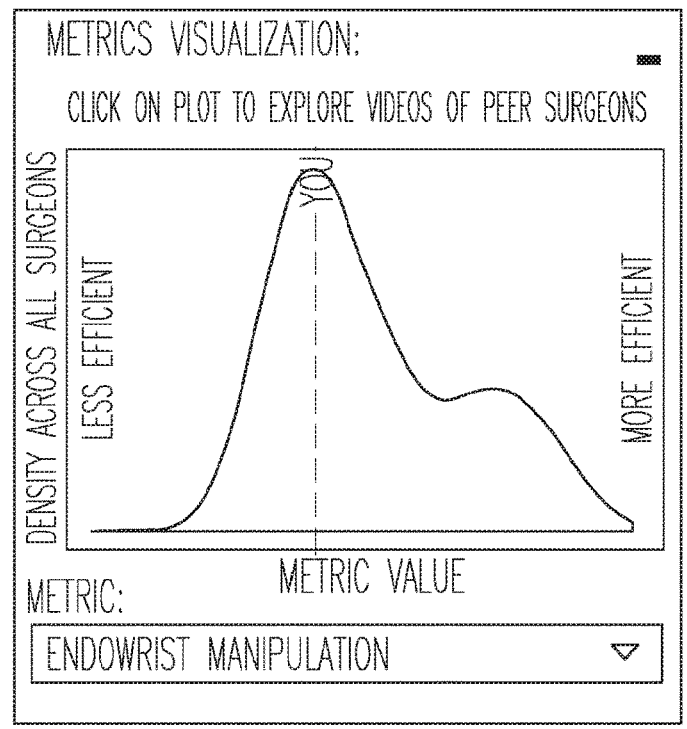
FIGS. 14A-14B are illustrative fifth performance metric-based motion picture selection user interface displays providing a fifth interactive visual index to select among a collection of motion pictures based upon a wrist manipulation metric.
Figure 14B:
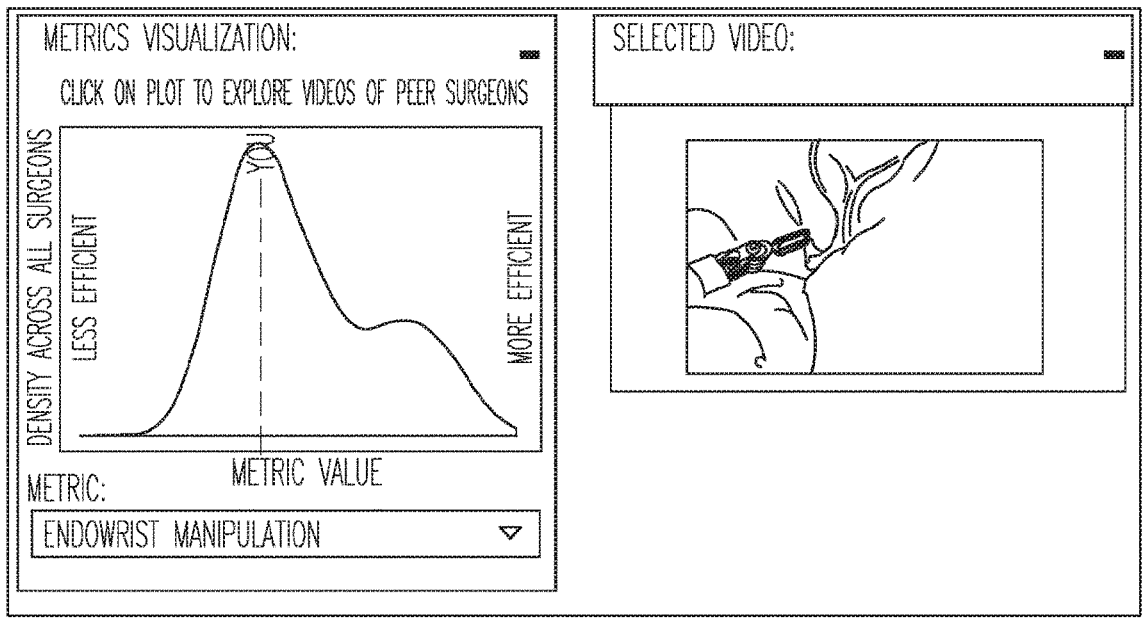

FIGS. 14A-14B are illustrative fifth metric-based motion picture selection user interface displays providing a fifth interactive visual index to select among a collection of motion pictures based upon a wrist manipulation metric. A user may use a pull-down menu to select the fifth metric-based motion picture selection user interface. The wrist manipulation metric represents a cumulative sum of wrist articulations for a user's left and right hand tools. Greater wrist articulation is more efficient. The motion pictures of the collection stored within the storage device 609 are additionally indexed based upon the fifth metric, also referred to herein as a wrist manipulation metric. More specifically, respective values may be determined for one or more parameters for each respective motion pictures of the collection. Respective wrist manipulation metric values for the respective motion pictures of the collection may be determined based upon corresponding respective values of the one or more parameters from Table 7. The wrist manipulation metric-based motion picture selection user interface of FIGS. 14A-14B2 includes a fifth histogram curve in which a vertical axis represents density of users across all users, who may be surgeons, and a horizontal axis represents cumulative wrist articulation. Increasing values on the vertical axis indicate a greater density of users at a corresponding performance level for the overall metric. Increasing metric values on the horizontal axis indicate greater cumulative wrist articulation, which is more efficient. A user who is more skilled according to the wrist manipulation metric has greater cumulative wrist articulation. A user may refer to the fifth meter of the comparative performance user interface of FIG. 9 to determine his or her personal value for the wrist manipulation metric. The fifth histogram provides a visual indication of a user's personal value relative to the values for the fifth metric of other users. A user may thereby determine how his or her performance as measured by the fifth metric compares with other users. Referring to FIG. 14B, there is shown an illustrative drawing showing a display of the fifth interactive visual index that includes a selection indicator indicating a user's selection of an indexed wrist manipulation metric value on the index and also showing a display of a motion picture from the collection of motion pictures, corresponding to the selected wrist manipulation value. Further details of user selection based upon the fifth interactive visual index will be understood from the discussion above.

Figure 15A:
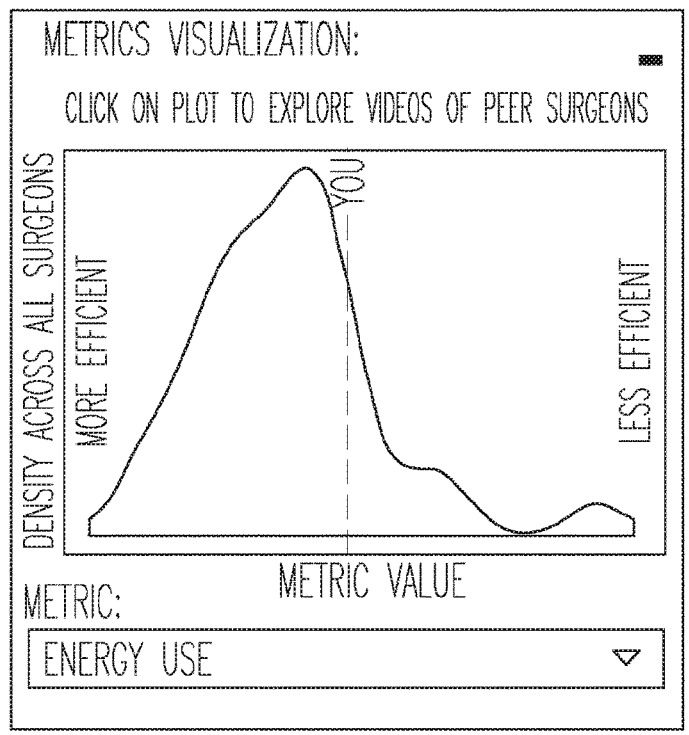
FIGS. 15A-15B are illustrative sixth performance metric-based motion picture selection user interface displays providing a sixth interactive visual index to select among a collection of motion pictures based upon an energy use metric.
Figure 15B:
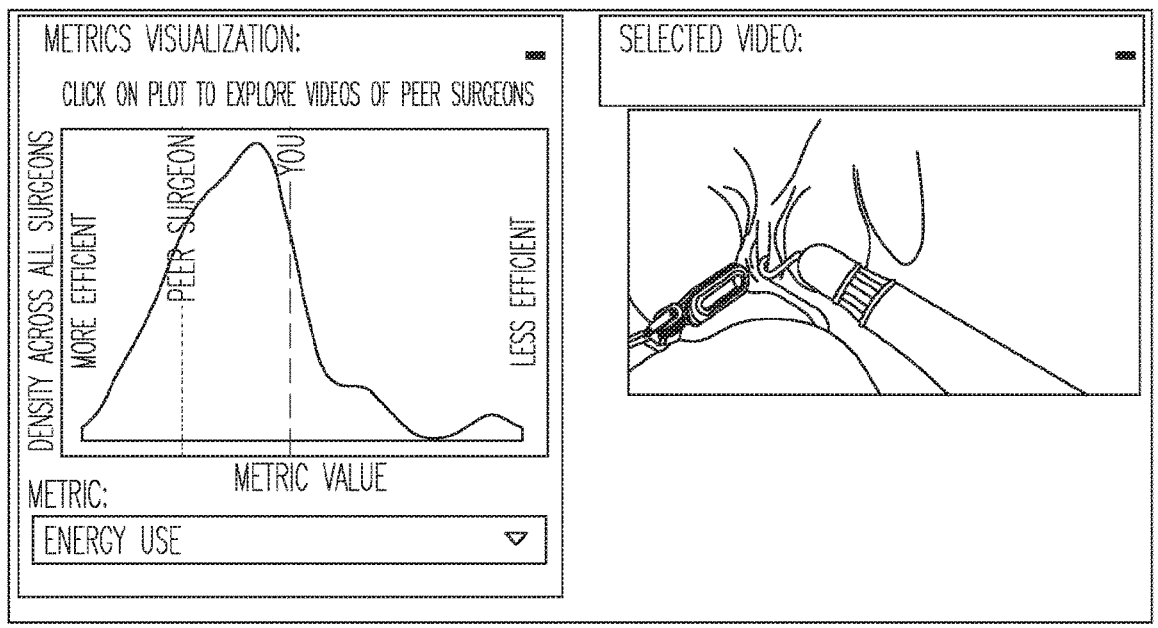

FIGS. 15A-15B are illustrative sixth metric-based motion picture selection user interface displays providing a sixth interactive visual index to select among a collection of motion pictures based upon an energy use metric. An energy-enabled tool, such as cautery, can be installed, for example, on an instrument arm, and energy activation is controlled by one or more of the pedals (Component 37). The relevant parameters here are simply the time when a pedal is depressed and when it is released. A user may use a pull-down menu to select the sixth metric-based motion picture selection user interface. The energy use metric represents a frequency of energy application, such as by cautery tools, for example. Less frequent energy use is more efficient. The motion pictures of the collection stored within the storage device 609 are additionally indexed based upon the sixth metric, also referred to herein as an energy use metric. More specifically, respective values may be determined for one or more parameters for each respective motion pictures of the collection. Respective energy use metric values for the respective motion pictures of the collection may be determined based upon corresponding respective values of the one or more parameters. For example, arm 1, 2, and 3, each with parameters of activation state and time of pedals (37)—if an energy instrument is installed on this arm. (No table shown). The energy use metric-based motion picture selection user interface of FIGS. 15A-15B includes a sixth histogram curve in which a vertical axis represents density of users across all users, who may be surgeons, and a horizontal axis represents frequency of energy use. Increasing values on the vertical axis indicate a greater density of users at a corresponding performance level for the overall metric. Increasing metric values on the horizontal axis indicate more frequent energy use, which is less efficient. A user who is more skilled according to the energy use metric has a lower frequency of energy use. A user may refer to the sixth meter of the comparative performance user interface of FIG. 9 to determine his or her personal value for the energy use metric. The sixth histogram provides a visual indication of a user's personal value relative to the values for the sixth metric of other users. A user may thereby determine how his or her performance as measured by the sixth metric compares with other users. Referring to FIG. 15B, there is shown an illustrative drawing showing a display of the sixth interactive visual index that includes a selection indicator indicating a user's selection of an indexed energy use metric value on the index and also showing a display of a motion picture from the collection of motion pictures, corresponding to the selected energy use value. Further details of user selection based upon the sixth interactive visual index will be understood from the discussion above.

Multiple other metrics can be included and selected by users. Additionally, the entire video of the task can be shown or just short clips that relate to the selected metrics (for example, if camera movement is selected, the user would see a clip of the relevant task with optimal use of camera by a peer surgeon).

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein. The above description is presented to enable any person skilled in the art to create and use a training system and method with user performance indexed to motion pictures. Various modifications to the embodiments will be readily apparent to those skilled in the art, and the generic principles defined herein may be applied to other embodiments and applications without departing from the scope of the invention. In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the scope of the invention, which is defined in the appended claims.

What is claimed is:

1. An apparatus to train users in manual control of motion imparted to input control components of a system, to control motion of one more tools of the system, that follow the motion of the input control components, comprising:
- a tangible machine-readable storage medium embodying a collection of respective motion pictures, which respectively show tool movement controlled by user input received at a control component input from corresponding respective users, indexed based upon corresponding respective user performance for a metric of the corresponding respective users controlling the tool movement shown in respective motion pictures;
- at least one hardware processor;
- a display screen; and
- a tangible machine-readable medium embodying a set of instructions that, when executed by the at least one hardware processor, cause the at least one processor to perform operations, the operations comprising:
  - generating a user interface on the display screen providing an interactive visual index to select respective motion pictures from the collection of respective motion pictures based upon corresponding respective user performance for the metric of corresponding respective users that controlled tool movement shown in the respective motion pictures; and
  - displaying on the display screen in response to receiving a user input selecting an index point of the interactive visual index, a motion picture from the collection of motion pictures, indexed by the index structure to a user performance level represented by the selected index point.

2. The apparatus of claim 1,
wherein the interactive visual index includes a graphical representation showing a relationship between density of users and user performance.

3. The apparatus of claim 1,
wherein the interactive visual index includes a graphical representation showing a relationship between density of users and user performance; and
wherein the index point includes a portion of the graphical representation.

4. The apparatus of claim 1,
wherein the interactive visual index includes a histogram indicating density of users at range user performance; and
wherein the index point includes a portion of the histogram.

5. The apparatus of claim 1, the operations further including:
generating on the display screen, an indication of an individual user's comparative performance with respect to the index.

6. An apparatus to train users in manual control of motion imparted to input control components of a system, to control motion of one more tools of the system, that follow the motion of the input control components, comprising:
- a display screen;
- at least one hardware processor;
- at least one sensor to sense a change in at least one of an actuation state and a position of at least one of the input control component and the tool;
- a tangible machine-readable storage medium embodying a collection of respective motion pictures, which respectively show tool movement imparted by the control component in response to manual input provided by corresponding respective users, indexed based upon corresponding respective user performance for at least one metric of the corresponding respective users;
- a tangible machine-readable medium embodying a set of instructions that, when executed by the at least one hardware processor, cause the at least one processor to perform operations, the operations comprising:
  - determining an individual user's performance for the at least one metric based at least in part upon a sensed change in the at least one of the actuation state and the position of the of at least one of the input control component and the tool;
  - recording a motion picture of the tool movement imparted by the control component in response to manual input provided by the individual user; and
  - indexing the recorded motion picture to the collection of motion pictures based upon the determined individual user's performance for the at least one metric.

7. The apparatus of claim 6,
wherein the at least one sensor is configured to sense a change in position of an end tip portion of a tool arm; and
wherein the processor is configured to determine a distance traveled by the end portion of the tool arm based upon the sensed change in position;
wherein determining the individual user's performance for the at least one metric includes determining based at least in part upon the determined distance traveled.

8. The apparatus of claim 6,
wherein the at least one sensor is configured to sense a change in position of at least a portion of the input control component; and
wherein the processor is configured to determine a three-dimensional volume within which the individual user's hand remains during a substantial portion of a time in which the individual user provides manual input to the master input control component;
wherein determining the individual user's performance for the at least one metric includes determining based at least in part upon the determined three-dimensional volume.

9. The apparatus of claim 6,
wherein the at least one sensor is configured to sense a change in position of a camera mounted at a tool; and
wherein the processor is configured to determine a number of changes in position of the camera;
wherein determining the individual user's performance for the at least one metric includes determining based at least in part upon the determined number of changes of camera position.

10. The apparatus of claim 6,
wherein the at least one sensor is configured to sense a change in position of a camera mounted at a tool; and
wherein the processor is configured to determine a frequency of changes in position of the camera;
wherein determining the individual user's performance for the at least one metric includes determining based at least in part upon the determined frequency of changes of camera position.

11. The apparatus of claim 6,
wherein the at least one sensor is configured to sense a change in manual user input from control of a tool arm to a different tool arm; and
wherein the processor is configured to determine a time delay between a user input indicating a change in manual user input from control of a tool arm to a different tool arm and movement of the different, tool arm;
wherein determining the individual user's performance for the at least one metric includes determining based at least in part upon the determined time delay between a user input indicating a change in manual user input from control of a tool arm to a different, tool arm and movement of the different tool arm.

12. The apparatus of claim 6,
wherein the at least one sensor is configured to sense successive movements to change a position of the tool; and
wherein the processor is configured to determine a time delay between successive movements of the tool;
wherein determining the individual user's performance for the at least one metric includes determining based at least in part upon the determined delay between successive movements of the tool.

13. The apparatus of claim 6,
wherein the at least one sensor is configured to sense a tool change in position from a position from to a different position; and
wherein the processor is configured to determine a speed at which the tool changes position from the position from to the different position;
wherein determining the individual user's performance for the at least one metric includes determining based at least in part upon the determined speed at which the tool changes position from the position from to the different position.

14. The apparatus of claim 6,
wherein the at least one sensor is configured to sense a change in angular position of a tool wrist from an angular position to a different angular position; and
wherein the processor is configured to determine an amount of angular rotation of the tool;
wherein determining the individual user's performance for the at least one metric includes determining based at least in part upon the determined amount of angular rotation of the tool based upon the sensed change from the angular position to a different angular position.

15. The apparatus of claim 6,
wherein determining the individual user performance includes determining based upon the sensed change applied to a machine learning model of the metric.

16. The apparatus of claim 6, further including:
wherein the tangible machine-readable medium embodying the set of instructions that, when executed by the at least one hardware processor, cause the at least one processor to perform operations, the operations further comprising:
generating a user interface on the display screen providing an interactive visual index to select respective motion pictures from the collection of respective motion pictures based upon corresponding respective user performance for the at least one metric of corresponding respective users that controlled tool movement shown in the respective motion pictures; and
displaying on the display screen in response to receiving a user input selecting an index point of the interactive visual index, a motion picture from the collection of motion pictures, indexed by the index structure to a user performance level represented by the selected index point.

17. A method to train users in manual control of motion imparted to input control components of a system to control motion of one more tools of the system that follow the motion of the input control components comprising:
storing in a tangible machine-readable storage medium, a collection of motion pictures, which show tool movement controlled by user input received at a control component input from corresponding respective users, indexed based upon corresponding respective user performance for a metric of the corresponding respective users controlling the tool movement shown in respective motion pictures;
generating a user interface on the display screen providing an interactive visual index to select respective motion pictures from the collection of respective motion pictures based upon corresponding respective user performance for the metric of corresponding respective users that controlled tool movement shown in the respective motion pictures; and
displaying on the display screen in response to receiving a user input selecting an index point of the interactive visual index, a motion picture from the collection of motion pictures, indexed by the index structure to a user performance level represented by the selected index point.

18. The method of claim 17,
wherein the interactive visual index includes a graphical representation showing a relationship between density of users and user performance.

19. The method of claim 17,
wherein the interactive visual index includes a histogram indicating density of users at range user performance.

20. The method of claim 17 further including:
receiving a user input at a manual input control component of the system to control movement of a tool;
sensing a change in a parameter value representing at least one of a change in an actuation state, a change in position, and a change in orientation of at least one of the input control component and the tool;
determining a user performance for a metric based at least in part upon the sensed change;
recording a motion picture of the tool movement; and
indexing the recorded motion picture to the collection of motion pictures based upon the determined user performance for the metric or a combination of multiple metrics.

* * * * *